United States Patent
Lee et al.

(10) Patent No.: US 9,683,042 B2
(45) Date of Patent: Jun. 20, 2017

(54) T-CELL-SPECIFIC HUMANIZED SINGLE FRAGMENT ANTIBODY DELIVERY VEHICLE

(71) Applicant: INDUSTRY-UNIVERSITY COOPERATION FOUNDATION HANYANG UNIVERSITY, Seoul (KR)

(72) Inventors: Sang Kyung Lee, Seoul (KR); Hyo Jeong Hong, Chuncheon-si (KR); Priti Kumar, Hamden, CT (US)

(73) Assignee: INDUSTRY-UNIVERSITY COOPERATION FOUNDATION, HANYANG UNIVERSITY, Seoul (KR)

( * ) Notice: Subject to any disclaimer, the term of this patent is extended or adjusted under 35 U.S.C. 154(b) by 0 days.

(21) Appl. No.: 14/654,273

(22) PCT Filed: Mar. 5, 2013

(86) PCT No.: PCT/KR2013/001760
§ 371 (c)(1),
(2) Date: Jun. 19, 2015

(87) PCT Pub. No.: WO2014/098319
PCT Pub. Date: Jun. 26, 2014

(65) Prior Publication Data
US 2016/0060341 A1    Mar. 3, 2016

(30) Foreign Application Priority Data
Dec. 20, 2012  (KR) .................. 10-2012-0149456

(51) Int. Cl.
*A61K 39/395*    (2006.01)
*C07K 16/28*    (2006.01)
(Continued)

(52) U.S. Cl.
CPC ........ *C07K 16/2803* (2013.01); *A61K 47/484* (2013.01); *A61K 47/48415* (2013.01);
(Continued)

(58) Field of Classification Search
None
See application file for complete search history.

(56) References Cited

U.S. PATENT DOCUMENTS 7,615,213 B2    11/2009  Kasaian et al.
2003/0004317 A1    1/2003  Johanson et al.
2010/0209440 A1    8/2010  Shankar et al.

FOREIGN PATENT DOCUMENTS

JP    2002-530108 A    9/2002
KR    2007-0022219 A    2/2007
(Continued)

OTHER PUBLICATIONS

Paul, Fundamental Immunology, 3rd Edition, 1993, pp. 292-295.*
(Continued)

*Primary Examiner* — Sheela J Huff
(74) *Attorney, Agent, or Firm* — Clark & Elbing LLP; Susan M. Michaud

(57) ABSTRACT

The present invention relates to a humanized scFv delivery vehicle targeted to be human T-cell specific, and provides: a humanized scFv which comprises a heavy-chain variable region (VH) consisting of a polypeptide comprising an amino acid sequence given by sequence number 32 and comprises a light-chain variable region (VL) consisting of a polypeptide comprising an amino acid sequence given by sequence number 34; and a T-cell-specific drug or marker delivery vehicle comprising the humanized scFv. The humanized scFv of the present invention has minimalised antigenicity and has an effect which does not give rise to an immune reaction even when used in the human body, and
(Continued)

thus can advantageously be used as a delivery vehicle for specifically delivering a target substance such as a siRNA gene or an immune reaction regulating protein to T-cells.

13 Claims, 19 Drawing Sheets

(51) Int. Cl.
*C12N 15/11* (2006.01)
*A61K 47/48* (2006.01)
*A61K 39/00* (2006.01)

(52) U.S. Cl.
CPC ...... *A61K 47/48561* (2013.01); *C12N 15/111* (2013.01); *A61K 2039/505* (2013.01); *C07K 2317/24* (2013.01); *C07K 2317/622* (2013.01); *C07K 2317/94* (2013.01); *C12N 2310/14* (2013.01); *C12N 2310/3513* (2013.01); *C12N 2320/32* (2013.01)

(56) References Cited

FOREIGN PATENT DOCUMENTS

| KR | 20100050438 A | 5/2010 |
| KR | 2011-0133716 A | 12/2011 |
| WO | WO-03/051926 A2 | 6/2003 |

OTHER PUBLICATIONS

Rudikoff et al(Proc. Natl. Acad. Sci. USA 1982 vol. 79: p. 1979).*
Pascalis et al (The Journal of Immunology (2002) 169, 3076-3084).*
Casset et al. (2003) BBRC 307, 198-205.*
Martin et al, Clinical Immunology vol. 148 p. 136 (2013).*
Hwang et al., "Use of human germline genes in a CDR homology-based approach to antibody humanization," Methods. 36(1):35-42 (2005).
International Search Report for International Application No. PCT/KR2013/001760, dated Aug. 23, 2013 (10 pages).

* cited by examiner mouse-derived antibody    humanized antibody

Fig. 4
Fig. 5
(A)
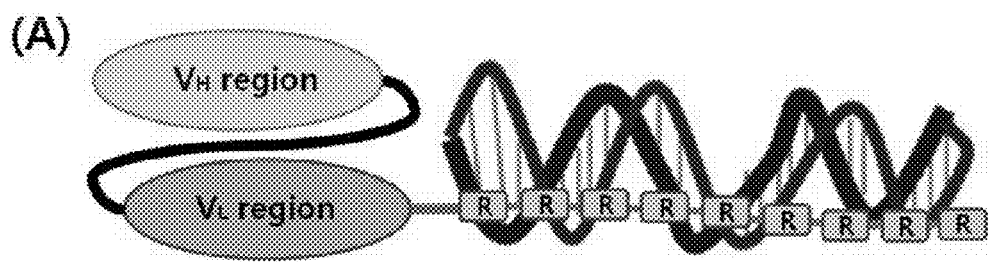
(B)
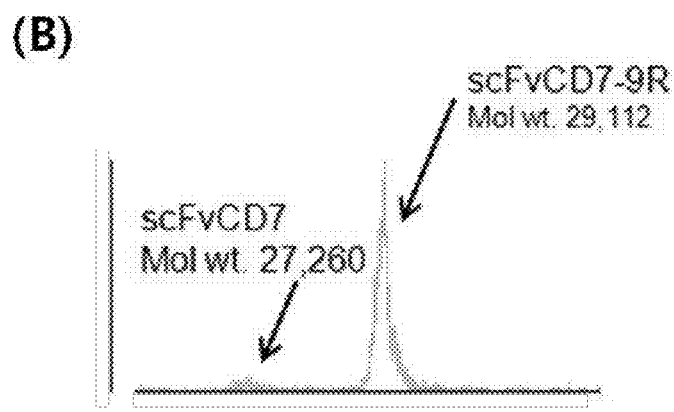

T-CELL-SPECIFIC HUMANIZED SINGLE FRAGMENT ANTIBODY DELIVERY VEHICLE

TECHNICAL FIELD

The present invention was made with the support of the Ministry of Knowledge Economy, Republic of Korea, under Project No. KT-2008-NT-AP-FS0-0001. This project was conducted in the program titled "Korea-US Technology Cooperation Program (KORUS Tech)" in the project named "the development of leukocyte-specific RNA interference nanodrug for treating AIDS" by the Industry-Academic Cooperation Foundation, Hanyang University, under management of the Korea Evaluation Institute of Industrial Technology, during the period of Dec. 1, 2008 to Nov. 30, 2011.

This application claims priority to and the benefit of Korean Patent Application No. 10-2012-0149456 filed in the Korean Intellectual Property Office on Dec. 20, 2012, the disclosure of which are incorporated herein by reference.

The present invention relates to a T cell-specific scFv carrier, and more specifically, to a humanized scFv carrier specifically targeting human T cells.

BACKGROUND ART

As modern societies are gradually aging together with the development of medical technology, age-related diseases with an increasing incidence are emerging as a new social problem. Autoimmune diseases, which are caused by abnormal immunomodulatory activity of immune cells of the human body, such as rheumatic disease or colon diseases, make up a large proportion of the age-related diseases. A method of modulating immune responses through immune cells, such as T cells or macrophagocytes, is receiving renewed attention as an alternative for the treatment of the autoimmune disease. The T cells play a very important role in the immune responses, and the immune responses can be modulated due to the cytokine secretion of T cells. Therefore, the above diseases can be treated by delivering siRNA gene or immune response modulating proteins to modulate immune responses. A T cell-specific carrier is used to deliver the siRNA gene or immune response modulating proteins to T cells, thereby modulating the immune responses of T cells and treating the above diseases.

Recently, studies about the use of antibodies are being conducted in order to deliver cell-specific therapeutic proteins or genes, and here, the specific binding of epitopes of the antibody to antigens is employed. Antibodies produced from rabbits, goats, and rodents are used, but since animal testing is performed on rodents in most study stages, rodent-derived antibodies are used more frequently. As a result of these studies, a muscFvCD7-9R carrier in which Oligo-9-Arginine (9R) binds to mouse-derived scFv (muscFvCD7) specifically binding to CD7, which is the T-cell surface protein, was manufactured. It was verified that, small interfering RNA (siRNA) capable of preventing the infection and replication of AIDS viruses is allowed to bind to the scFvCD7-9R carrier, thereby delivering anti-virus siRNA specifically to T cells, and suppressing replication of viruses, which are previously present in vivo, including the infection and replication of AIDS viruses (Kumar et al., Cell, 2008 Aug. 22; 134(4):577-586).

Nevertheless, CD7-specific scFv (muscFvCD7) used in conventional studies by Kumar et al. (2008) is derived from a rodent (*Mus musculus*), and exhibits antigenicity in vivo when applied to the humanized mouse or the human body. The carrier having antigenicity as above may cause an immune response in vivo prior to cell-specific delivery of siRNA gene or immune response modulating protein, lowering efficiency of delivering siRNA gene or immune response modulating protein into T cells. Therefore, a humanized single chain antibody for using the foregoing rodent-derived scFv as a carrier needs to be developed.

Throughout the entire specification, many papers and patent documents are referenced and their citations are represented. The disclosures of cited papers and patent documents are entirely incorporated by reference into the present specification, and the level of the technical field within which the present invention falls and details of the present invention are explained more clearly.

DETAILED DESCRIPTION OF THE INVENTION

Technical Problem

An aspect of the present invention is to provide humanized scFv specifically targeting human T cells without exhibiting antigenicity in the body, and a carrier of a drug or label using the same.

Other purposes and advantages of the present disclosure will become more obvious with the following detailed description of the invention, claims, and drawings.

Technical Solution

In accordance with an aspect of the present invention, there is provided a humanized scFv including a heavy chain variable region ($V_H$) composed of a polypeptide including an amino acid sequence represented by SEQ ID NO: 32, and a light chain variable region ($V_L$) composed of a polypeptide including an amino acid sequence represented by SEQ ID NO: 34.

In accordance with another aspect of the present invention, there is provided a carrier for delivering a drug or label specifically to T cells by targeting the T cells, the carrier including the humanized scFv.

Hereinafter, the present invention will be described in detail.

1. Humanized scFv to Human CD7 (HzscFvCD7) and Vector Expressing same

An aspect of the present invention provides a humanized scFv comprising a heavy chain variable region ($V_H$) composed of a polypeptide including an amino acid sequence represented by SEQ ID NO: 32, and a light chain variable region ($V_L$) composed of a polypeptide including an amino acid sequence represented by SEQ ID NO: 34.

Another aspect of the present invention provides a heavy chain variable region ($V_H$) of a T cell-specific humanized antibody, composed of a polypeptide including an amino acid sequence represented by SEQ ID NO: 32 and a light chain variable region ($V_L$) of the T cell-specific humanized antibody, composed of a polypeptide including an amino acid sequence represented by SEQ ID NO: 34.

Still another aspect of the present invention provides a recombinant vector including a nucleotide sequence coding the humanized scFv.

The humanized scFv of the present invention includes a heavy chain variable region ($V_H$) of a T cell-specific humanized antibody and a light chain variable region ($V_L$) of the T cell-specific humanized antibody.

Each of the heavy chain variable region (V_H) and the light chain variable region (V_L) of the T cell-specific humanized antibody includes three complementarity determining regions (hereinafter referred to as CDR) and four frameworks (hereinafter, referred to FR), which are arranged in the order of "FR1-CDR1-FR2-CDR2-FR3-CDR3-FR4" from the N-terminal to the C-terminal of the heavy chain variable region (V_H) and the light chain variable region (V_L).

Preferably, the heavy chain variable region (V_H) of the humanized antibody is configured such that amino acid sequences of FRs and CDRs have high identity to FRs of the human heavy chain sequence, especially, IGHV3-h*01(P), and CDRs of the non-human-derived antibody to human CD7, respectively. More preferably, the heavy chain variable region (V_H) of the humanized antibody is composed of a polypeptide including an amino acid sequence represented by SEQ ID NO: 32. Most preferably, the heavy chain variable region (V_H) of the humanized antibody is composed of a polypeptide including an amino acid sequence coded with a nucleotide sequence represented by SEQ ID NO: 33. However, the heavy chain variable region (V_H) of the humanized antibody is not limited thereto, and includes various variants derived from the amino acid sequence represented by SEQ ID NO: 32 while having both complementarity specific to T cells and the minimum antigenicity to a human immune system. In a specific embodiment of the present invention, the heavy chain variable region (V_H) having an amino acid sequence represented by SEQ ID NO: 32 was designed by combining CDRs of the mouse-derived antibody to human CD7 (CD7cys) and FRs of IGHV3-h*01 (P), which is a human heavy chain sequence, and arranging the CDRs and the FRs in the order of "FR1-CDR1-FR2-CDR2-FR3-CDR3-FR4" (see FIG. 1).

Preferably, the light chain variable region (V_L) of the humanized antibody is configured such that amino acid sequences of FRs and CDRs have high identity to FRs of the human light chain sequence, especially, IGKV1-27*01, and CDRs of the non-human-derived antibody to human CD7, respectively. More preferably, the light chain variable region (V_L) of the humanized antibody is composed of a polypeptide including an amino acid sequence represented by SEQ ID NO: 34. Most preferably, the light chain variable region (V_L) of the humanized antibody is composed of a polypeptide including an amino acid sequence coded with a nucleotide sequence represented by SEQ ID NO: 35. However, the light chain variable region (V_L) of the humanized antibody is not limited thereto, and includes various variants derived from the amino acid sequence represented by SEQ ID NO: 34 while having both complementarity specific to T cells and the minimum antigenicity to a human immune system. In a specific embodiment of the present invention, the light chain variable region (V_L) having an amino acid sequence represented by SEQ ID NO: 34 was designed by combining CDRs of the mouse-derived antibody to human CD7 (CD7cys) and FRs of IGKV1-27*01, which is a human light chain sequence, and arranging the CDRs and the FRs in the order of "FR1-CDR1-FR2-CDR2-FR3-CDR3-FR4" (see FIG. 1).

The humanized scFv of the present invention preferably includes a heavy chain variable region (V_H) composed of a polypeptide including an amino acid sequence represented by SEQ ID NO: 32, and a light chain variable region (V_L) composed of a polypeptide including an amino acid sequence represented by SEQ ID NO: 34. Especially, preferably, the heavy chain variable region (V_H) is coded with a gene construct including a nucleotide sequence represented by SEQ ID NO: 33, and the light chain variable region (V_L) is coded with a gene construct including a nucleotide sequence represented by SEQ ID NO: 35, but are not limited thereto.

The humanized scFv is not particularly limited as long as it includes various variants derived from an amino acid sequence represented by SEQ ID NO: 36 while having both complementarity specific to T cells and the minimum antigenicity to a human immune system. However, preferably, the humanized scFv is composed of a polypeptide including an amino acid sequence represented by SEQ ID NO: 36. More specifically, the humanized scFv is coded with a gene construct including a nucleotide sequence coding an amino acid sequence represented by SEQ ID NO: 36. Most preferably, the humanized scFv is coded with a gene construct including a nucleotide sequence represented by SEQ ID NO: 37. However, the humanized scFv is not limited thereto.

The gene construct coding the humanized scFv, more preferably, the gene construct including a nucleotide sequence represented by SEQ ID NO: 37 may be included in an expression vector. The humanized scFv may be repeatedly mass-produced by using the vector. Besides, in cases where a recombinant protein in which the humanized scFv is fused with a heterologous protein needs to be prepared, a polynucleotide coding the heterologous protein is inserted into a multi-closing site (MCS) of the expression vector including the gene construct, thereby mass-producing the recombinant protein in which the humanized scFv is fused with the heterologous protein.

Since the humanized scFv is designed to have high identity to the CDRs of the non-human-derived antibody to human CD7, the humanized scFv also has complementarity specifically to human CD7. Since the CD7 is a protein that is specifically expressed on surfaces of human T cells, the humanized scFv of the present invention specifically binds to human T cells, ultimately.

In addition, the humanized scFv is designed to have high identity to FRs of human-derived heavy chain and light chain sequences, and thus exhibits the minimum antigenicity to a human immune system. Therefore, the humanized scFv can be applied to the human body without a particular immune rejection reaction.

In a specific embodiment of the present invention, recombinant PCR is repeatedly performed to finally prepare HzscfvCD7-pET21b expression vector including a nucleotide sequence represented by SEQ ID NO: 37 (see FIG. 3), and the expression vector is expressed and purified in *E. coli* strain BL21 to give about 27-kDa HzscFvCD7 composed of an amino acid sequence represented by SEQ ID NO: 36 (see FIG. 4). (1) In vitro competition assay on the thus prepared HzscFvCD7 and the conventional muscFvCD7 (Kumar et al., Cell, 2008 Aug. 22; 134(4):577-586) verified that HzscFvCD7 and muscFvCD7 recognize the same antigen (see FIG. 11). (2) It was verified in vivo that the thus prepared HzscFvCD7 is injected into the humanized mouse (Hu-HSC) to specifically bind to the CD7 protein of CD45+/CD3+ human T cells, more accurately, the CD protein of human T cells (see FIGS. 12 to 14). (3) It was verified in vivo that siFITC (FITC-conjugated CD4 siRNA) or poly (lactic-co-glycolic acid) (PLGA) is specifically delivered to human T cells by the thus prepared HzscFvCD7 in the humanized mouse (Hu-PBL) (see FIGS. 15 and 16). Furthermore, pharmacokinetic assay verified that the specificity of HzscFvCD7 to T cells is superior to that of the previously humanized antibody/scFv (see FIG. 17 and table 1). Furthermore, as a result of in vitro measuring the degree of antigenicity of HzscFvCD7 in the body by using a human anti-mouse antibody (HAMA), the immune response by the HAMA gradually decreased as the HAMA is further diluted, and the immune response decreased by approximately 70% when the HAMA is diluted at 1:100 (see FIG. 18). The above results verified in vitro that the antigenicity in the body significantly decreased in the HzscFvCD7 rather than in the conventional mAbCD7 and muscFvCD7 (Kumar et al., Cell, 2008 Aug. 22; 134(4):577-586). Furthermore, it was verified that, as a result of measuring the degree of induction of differentiation and proliferation of pancreatic cells by injecting the thus prepared HzscFvCD7 into the humanized mouse (Hu-BLT), HzscFvCD7 did not really induce the differentiation and proliferation of pancreatic cells in the humanized mouse (see FIGS. 19 and 20).

2. Carrier Including HzscFvCD7

Still another aspect of the present invention provides a carrier for delivering a T-cell activity regulator or a label specifically to T cells by targeting T cells, the carrier including the humanized scFv described in "1. Humanized scFv to human CD (HzscFvCD7) and vector expressing same" above.

Still another aspect of the present invention provides a composition for diagnosing T cell-mediated diseases, the composition containing the humanized scFv; and a label fused to the N-terminal or C-terminal of the scFv.

Still another aspect of the present invention provides a pharmaceutical composition for diagnosing T cell-mediated diseases, the pharmaceutical composition containing the humanized scFv; and a T-cell activity regulator fused to the N-terminal or C-terminal of the scFv.

The humanized scFv are the same as described in "1. Humanized scFv to human CD (HzscFvCD7) and vector expressing same" above. Therefore, detailed descriptions thereof will be omitted by citing the descriptions of "1. Humanized scFv to human CD (HzscFvCD7) and vector expressing same" above, and hereinafter, only particular features of the carrier and composition will be described.

The scFv described in "1. Humanized scFv to human CD (HzscFvCD7) and vector expressing same" can be applied to the human body without a particular immune rejection reaction while having complementarity to specifically bind to human T cells, and thus can be used as a carrier for specifically delivering a T-cell activity regulator or a label to T cells.

(1') When a label binds to the scFv, the scFv can specifically label only T cells. Therefore, the scFv and label fused product can be used as a composition for diagnosing T cell-mediated diseases. Furthermore, (2') when a T-cell activity regulator binds to the scFv, the scFv can deliver the T-cell activity regulator specifically to T cells, and thus the scFv and T-cell activity regulator fused product can be used as a pharmaceutical composition for preventing or treating T cell-mediated diseases.

According to another aspect of the present invention, the present invention provides a method for preventing or treating T cell-mediated diseases, the method comprising administering to a subject a composition containing a pharmaceutically effective amount of a T-cell activity regulator fused on the N-terminal or C-terminal of the humanized scFv of the present invention.

The composition for diagnosing T cell-mediated diseases of the present invention contains a label fused on the N-terminal or C-terminal of the humanized scFv of the present invention.

Since the humanized scFv are the same as described in "1. Humanized scFv to human CD (HzscFvCD7) and vector expressing same", detailed descriptions thereof will be omitted.

The label is for detecting and quantifying T cells, and may be at least one selected from the group consisting of chromogenic enzymes (peroxidase, alkaline phosphatase, etc.), fluorescent materials (FITC, RITC, rhodamine, Texas Red, fluorescein, phycoerythrin, and quantum dots), chromophores, and radioactive isotopes ($^{124}$I, $^{125}$I, $^{111}$In, $^{99m}$Tc, $^{32}$P, $^{35}$S, etc.). In cases where the label is fused on the scFv, the label is preferably fused so as to avoid an influence on specificity or selectivity of the scFv to T cells. To this end, the label may be directly linked (covalent linkage or cross-linkage) to the scFv or may be indirectly fused through a linker (9R3L, 18R6L, liposome, etc.). The fused location of the label can be easily determined by a person skilled in the art through repeated tests.

Since the label-fused scFv targets T cells, the scFv specifically binds to T cells when the composition is injected into the human body, and thus the location or amount of the label fused on the scFv are measured to diagnose T cell-mediated diseases.

The T cell-mediated disease may be at least one selected from the group consisting of acquired immunodeficiency syndrome (AIDS), graft rejection, graft-versus-host disease, unwanted delayed type of hypersensitivity reactions, T cell-mediated pulmonary diseases, and autoimmune diseases. More specifically, the T cell-mediated disease may be at least one selected from the group consisting of acquired immunodeficiency syndrome (AIDS), multiple sclerosis, neuritis, polymyositis, psoriasis, vitiligo, Sjogren's syndrome, rheumatoid arthritis, type 1 diabetes, autoimmune pancreatitis, inflammatory bowel disease, Crohn's disease, ulcerative colitis, celiac disease, glomerulonephritis, scleroderma, sarcoidosis, autoimmune thyroid disease, Hashimoto's thyroiditis, Graves' disease, myasthenia gravis, Addison's disease, autoimmune uveoretinitis, pemphigus vulgaris, primary biliary cirrhosis, pernicious anemia, and systemic lupus erythematosis.

The pharmaceutical composition for treating T cell-mediated diseases of the present invention contains a T-cell activity regulator fused on the N-terminal or C-terminal of the humanized scFv.

Since the humanized scFv are the same as described in "1. Humanized scFv to human CD (HzscFvCD7) and vector expressing same", detailed descriptions thereof will be omitted.

The T-cell activity regulator may be a T-cell activity inhibitor or a T-cell activity enhancer. In cases where the T-cell activity regulator is fused on the scFv, the T-cell activity regulator is preferably fused so as to avoid an influence on specificity or selectivity of the scFv to T cells. To this end, the T-cell activity regulator may be directly linked (covalent linkage or cross-linkage) to the scFv or may be indirectly fused through a linker (9R or liposome). The fused location of the T-cell activity regulator can be easily determined by a person skilled in the art through repeated tests.

In cases where the T-cell activity regulator is a T-cell activity inhibitor, the T-cell activity inhibitor may be antisense nucleotide, small interfering RNA (siRNA), short hairpin RNA (shRNA), or the like. The pharmaceutical composition containing the T-cell activity inhibitor can be used for the treatment of diseases caused by hyperactivity due to hyper-differentiation and hyper-proliferation of T cells. The diseases caused by the hyperactivity of T cells may be graft rejection, graft-versus-host disease, unwanted delayed type of hypersensitivity reactions, T cell-mediated pulmonary diseases, and autoimmune diseases. More specifically, the diseases may be multiple sclerosis, neuritis, polymyositis, psoriasis, vitiligo, Sjogren's syndrome, rheumatoid arthritis, type 1 diabetes, autoimmune pancreatitis, inflammatory bowel disease, Crohn's disease, ulcerative colitis, celiac disease, glomerulonephritis, scleroderma, sarcoidosis, autoimmune thyroid disease, Hashimoto's thyroiditis, Graves' disease, myasthenia gravis, Addison's disease, autoimmune uveoretinitis, pemphigus vulgaris, primary biliary cirrhosis, pernicious anemia, and systemic lupus erythematosis.

The antisense nucleotide binds to (hybridizes with) a complementary nucleotide sequence of DNA, unmatured-mRNA, or matured mRNA, as defined in Watson-Crick base pairs, to interrupt the flow of genetic information from DNA to proteins. The antisense nucleotide is a long chain of monomer units, and may be easily synthesized with respect to a target RNA sequence. Many recent studies validated the usefulness of the antisense nucleotide as a biochemical unit for researching target proteins (Rothenberg et al., J. Natl. Cancer Inst., 81:1539-1544, 1999). Since many advances have been recently made in fields of oligonucleotide chemistry, and synthesis of nucleotides exhibiting improved cell adhesion, target binding affinity, and nuclease resistance, the antisense nucleotide may be considered to be used as a novel type inhibitor.

The small interfering RNA (siRNA) complementarily binds to (hybridizes with) mRNA coding a target polypeptide in cells, thereby interrupting the flow of genetic information of the target polypeptide from DNA to proteins. The small interfering RNA (siRNA) is composed of a 15- to 30-nt sense sequence selected from the mRNA nucleotide sequence of any one gene expressed in T cells, and an antisense sequence complementarily binding to the sense sequence. The sense sequence is not particularly limited thereto, but is preferably composed of a 25-nt polynucleotide sequence.

The short hairpin RNA (shRNA) means a full-length RNA molecule including a 50- to 100-nt single strand RNA forming a stem-loop structure in cells, 15- to 50-nt new RNAs in base pairs, which complementarily bind to both sides of the loop region of a 5- to 30-nt (nucleotides), forming a double-strand stem, and further including 1- to 500-nt (nucleotides) before and after the stem forming strand. The loops of the shRNA are cut in cells, and the shRNA interrupts the flow of genetic information of the target polypeptide from DNA to protein, like siRNA. After the shRNA is cut in cells, the shRNA preferably has a 15- to 30-nt sense sequence selected from the mRNA nucleotide sequence of any one gene expressed in T cells and an antisense sequence complementarily binding to the sense sequence, but is not limited thereto.

In cases where the T-cell activity regulator is a T-cell activity enhancer, the T-cell activity enhancer may be an antiviral agent, such as Zidovudine, Didanosine, Zalcitabine, Stavudine, Lamivudine, Nevirapine, Delavirdine, Ritonavir, Indinavir, or Nelfinavir. The pharmaceutical composition containing the T-cell activity enhancer may be used to treat diseases caused by the degradation in T-cell activity, and a representative example of the disease caused by the degradation in T-cell activity may be acquired immunodeficiency syndrome (AIDS).

In preferable examples of the present invention, CD4 siRNA (siCD4) or FITC-conjugated siCD4 (siFITC) was fused to HzscFvCD7 using a linker, such as 9R or liposome, thereby preparing a complex having a structure as shown in FIG. 5 or 6 (see FIGS. 5 and 6). The prepared complex was used to treat Jurkat cells as T cells, or human peripheral blood mononuclear cells, thereby measuring the efficiency of introduction of siFITC into cells and the inhibition rate of expression of CD4 expressed one the cell surface. As a result, siFITC was introduced into Jurkat cells with high efficiency by HzscFvCD7-9R (see FIG. 7(A)), the CD4 expression was silenced in Jurkat cells and human peripheral blood mononuclear cells by siCD4 delivered by HzscFvCD7-9R (see FIG. 7(B) and FIG. 8), and the CD4 expression was silenced in Jurkat cells by siCD4 delivered by the HzscFvCD7-liposome (see FIG. 9). In addition, it was verified that protein GFP and polymer PLGA binding to HzscFvCD7 are specifically targeted in Jurkat cells (see FIG. 10). It can be seen from the above results that HzscFvCD7 of the present invention can be used to regulate T-cell activity by delivering a T-cell activity regulator, such as siRNA, specifically to T ells.

The pharmaceutical composition contains a fused product of the scFV and the T-cell activity regulator in, preferably, 0.0001 to 50 wt % based on the total weight of the composition, but is not limited thereto. In addition, the pharmaceutical composition may further include at least one pharmaceutically acceptable carrier in addition to the foregoing active ingredients, for administration. The pharmaceutically acceptable carrier may be at least one selected from a saline solution, sterile water, Ringer's solution, buffered saline, a dextrose solution, a maltodextrin solution, glycerol, ethanol, and liposome, and if necessary, other common additives, such as an antioxidant, a buffer solution, and a bacteriostatic agent, may be added to the pharmaceutical composition. Also, a diluent, a dispersant, a surfactant, a binder, and a lubricant are additionally added to the composition, which may be then formulated into an injectable dosage form, such as an aqueous solution, a suspension, or an emulsion, a pill, a capsule, or a tablet. A target organ specific antibody for specifically acting on a target organ, or other ligand may be used by binding to the carrier. Furthermore, the pharmaceutical composition may be preferably formulated according to the disease or ingredient, by using a suitable method in the art or a method disclosed in the document by Remington (Remington's Pharmaceutical Science (recent edition), Mack Publishing Company, Easton Pa.).

An administration method of the pharmaceutical composition may be orally administered or parenterally administered (for example, intravenous, subcutaneous, intraperitoneal, brain, or topical application), but is not particularly limited thereto. Here, the parenteral administration is preferable, and the direct injection to the midbrain is most preferable, but the administration method is not particularly limited thereto.

In addition, the dose of the pharmaceutical composition administered to the human body may vary depending on the age, body weight, and gender of the patient, the manner of administration, the health condition, and the severity of the disease. Based on the adult patient weighting 70 Kg, the dose thereof is generally 0.1 to 1,000 mg/day, and preferably 1 to 500 mg/day. The unit formulation may contain the daily dose or ½, ⅓, ¼ of the daily dose of the pharmaceutically composition. The pharmaceutical composition may be administered once a day or divided into one to six times at predetermined time intervals according to the judgment of the doctor or pharmacist.

Advantageous Effects

The humanized scFv of the present invention has minimized antigenicity, and thus does not cause an immune response even when applied to the human body, so that the humanized scFv of the present invention can be favorably used as a carrier for delivering a target material, such as siRNA gene or an immune response modulating protein specifically to T cells.

Meanwhile, the effects of the present invention are not limited to the above-mentioned effects, and other effects could be understood from the following descriptions by a person skilled in the art.

BRIEF DESCRIPTION OF THE DRAWINGS

FIGS. 1(A) and 1(B) illustrate that amino acid sequences of heavy chain sequence (SEQ ID NO: 32) and light chain sequence (SEQ ID NO: 34) of humanized antibody are designed by comparing mouse-derived antibody to human CD7 (CD7cys) (heavy chain sequence SEQ ID NO: 57 (A), and light chain sequence SEQ ID NO: 58 (B)) with human Ig germ line IGHV3-h*01 heavy chain sequence (SEQ ID NO: 59) (A), and human Ig germ line IGKV1-27*01 light chain sequence (SEQ ID NO: 60) (B), and FIG. 1(C) illustrates mouse-derived antibody and humanized antibody.

FIG. 4 is an SDS-PAGE gel image of HzscFvCD7 obtained through expression and purification E. coli BL21.

FIG. 5(A) is a schematic view showing a structure of a complex in which polyoligo-9-arginine (9R) binds to the C-terminal of HzscFvCD7, and FIG. 5(B) is a graph showing MALDI-TOF results confirming whether polyoligo-9-arginine (9R) bound to HzscFvCD7.

FIG. 12(A) shows graphs of FACS results confirming whether human CD45+ cells were present in blood, liver, thymus, and brain, and FIG. 12(B) shows a graph illustrating cell count in respective tissues of six mice.

FIG. 13(A) shows graphs confirming that human CD45+ cells were present in blood of Hu-HSC; FIG. 13(B) shows graphs confirming that HzscFvCD7 did not bind to mouse CD45+ cells; and FIG. 13(C) shows graphs confirming that HzscFvCD7 specifically bound to human CD45+ cells.

FIG. 14(A) shows graphs confirming the percentage of CD3+ T cells in human CD45+ cells in blood of Hu-HSC; FIG. 14(B) shows graphs confirming that HzscFvCD7 specifically bound to CD3+ T cells; and FIG. 14(C) shows graphs confirming that HzscFvCD7 did not bind to CD3− cells without CD3 expression, among CD45+ human cells.

MODE FOR CARRYING OUT THE INVENTION

Hereinafter, the present invention will be described in detail with reference to examples. These examples are only for illustrating the present invention more specifically, and it will be apparent to those skilled in the art that the scope of the present invention is not limited by these examples.

EXAMPLE 1

Preparation of Humanized scFv to Human CD7 (HzscFvCD7)

<1-1> Design of HzscFvCD7

Figures 1, 1B, 1C:
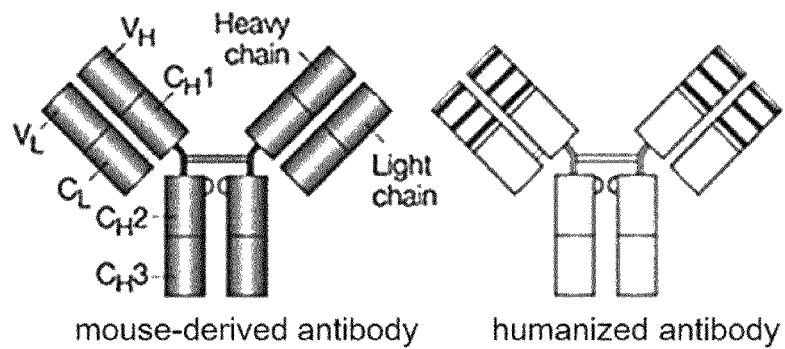

As a result of searching human germ cell lines having the highest amino acid sequence identity to a mouse-derived antibody to human CD7 (CD7cys) through the IMGT site (img.org), (1)the heavy chain sequence of the mouse-derived antibody to human CD7 (CD7cys) was most similar to IGHV3-h*01(P) of the human heavy chain sequence, and (2) the light chain sequence of the mouse-derived antibody to human CD7 (CD7cys) was most similar to IGKV1-27*01 of the human light chain sequence. Based on the above results, humanized scFv to CD7 (HzscFvCD7) was designed by replacing framework (FR) regions with human heavy chain or light chain sequence while conserving CDRs (in CDR of the antibody, the most variable region is referred to as hyper variable (HV) region, and a region of which the amino acid sequence is less changed and stable is referred to as FR) (FIG. 1). However, when designing the HzscFvCD7, portions of the FR regions that influence the structure or affinity of scFv were maintained as the sequence of the mouse-derived antibody as it is without being replaced with the human heavy or light chain sequence.

As a result, the heavy chain sequence of HzscFvCD7, which has an amino acid sequence of SEQ ID NO: 32, (HzCD7cys in FIG. 1(A)), and the light chain sequence of HzscFvCD7, which has an amino acid sequence of SEQ ID NO: 34, (HzCD7cys in FIG. 1(A)), were designed.

<1-2> Preparation of Humanized Heavy Chain and Light Chain Variable Regions Using Whole IgG Vector <1-2-1> Synthesis of Nucleotide Sequence of Humanized Heavy Chain Variable Region First, in order to synthesize a signal sequence of a heavy chain gene having a nucleotide sequence of SEQ ID NO: 38, PCR was performed using pdCMV-dhfr-AKA/HzK (Korean Patent Registration No. 10-0318761) as a template and LHS39 primer represented by SEQ ID NO: 1 and HCleaderBack primer represented by SEQ ID NO: 2 in a pair.

Then, in order to synthesize a heavy chain variable region of a mouse-derived antibody to human CD7, which has a nucleotide sequence of SEQ ID NO: 39, PCR was performed using scfvCD7-pET21b (prepared by PCR-amplifying pAK400scFvCD7-GFP construct (Matthias Peipp et al., CANCER RESEARCH 62, 2848-855, May 15, 2002) obtained from Dr. George Fey according to the coding sequence of scFvCD7 so as to s-s (disulfide) conjugate with a positively charged siRNA binding moiety, using a primer into which the C-terminal cysteine residue is introduced, and then cloning the PCR-amplified scFvCD7Cys into pET21b vector (Cat#69741-3, Novagen, US) as a template and CD7H-F primer represented by SEQ ID NO: 3 and CD7H-R primer represented by SEQ ID NO: 4 in a pair.

In order to humanize the thus obtained heavy chain variable region of the mouse-derived antibody to human CD7, which has the nucleotide sequence of SEQ ID NO: 39, (1) "humanized heavy chain variable region fragment 1" having a nucleotide sequence of SEQ ID NO: 40 was obtained by performing PCR using CD7H-F primer represented by SEQ ID NO: 3 and CD7H1-R primer represented by SEQ ID NO: 6; (2) "humanized heavy chain variable region fragment 2" having a nucleotide sequence of SEQ ID NO: 41 was obtained by performing PCR using CD7H1-F primer represented by SEQ ID NO: 5 and CD7H2-R primer represented by SEQ ID NO: 8; (3) "humanized heavy chain variable region fragment 3" having a nucleotide sequence of SEQ ID NO: 42 was obtained by performing PCR using CD7H2-F primer represented by SEQ ID NO: 7 and CD7H3-R primer represented by SEQ ID NO: 10; (4) "humanized heavy chain variable region fragment 4" having a nucleotide sequence of SEQ ID NO: 43 was obtained by performing PCR using CD7H3-F primer represented by SEQ ID NO: 9 and CD7H4-R primer represented by SEQ ID NO: 12; (5) "humanized heavy chain variable region fragment 5" having a nucleotide sequence of SEQ ID NO: 44 was obtained by performing PCR using CD7H4-F primer represented by SEQ ID NO: 11 and CD7H5-R primer represented by SEQ ID NO: 14; and (6) "humanized heavy chain variable region fragment 6" having a nucleotide sequence of SEQ ID NO: 45 was obtained by performing PCR using CD7H5-F primer represented by SEQ ID NO: 13 and CD7H6-R primer represented by SEQ ID NO: 15.

In order to ligate the thus obtained six nucleotide sequence fragments of the humanized heavy chain variable region to human CD7, recombinant PCR was performed using "humanized heavy chain variable region fragment 1", "humanized heavy chain variable region fragment 2", and "humanized heavy chain variable region fragment 3" as templates and CD7H-F primer represented by SEQ ID NO: 3 and CD7H3-R primer represented by SEQ ID NO: 10, thereby obtaining "humanized heavy chain variable region fragment 1-1" having a nucleotide sequence of SEQ ID NO: 46. In addition, recombinant PCR was performed using "humanized heavy chain variable region fragment 4", "humanized heavy chain variable region fragment 5", and "humanized heavy chain variable region fragment 6" as templates and CD7H3-F primer represented by SEQ ID NO: 9 and CD7H6-R primer represented by SEQ ID NO: 15, thereby obtaining "humanized heavy chain variable region fragment 1-2" having a nucleotide sequence of SEQ ID NO: 47. Then, recombinant PCR was performed using the thus obtained humanized heavy chain variable region fragments 1-1 and 1-2 as templates and CD7H-F primer represented by SEQ ID NO: 3 and CD7H-R primer represented by SEQ ID NO: 4, thereby preparing a nucleotide sequence of the humanized heavy chain variable region to human CD7 of SEQ ID NO: 33.

Then, recombinant PCR was performed using the thus obtained signal sequence of SEQ ID NO: 38 and humanized heavy chain variable region to human CD7 of SEQ ID NO: 33 as templates and LHS39 primer represented by SEQ ID NO: 1 and CD7H-R primer represented by SEQ ID NO: 4, to ligate the signal sequence of SEQ ID NO: 38 and the humanized heavy chain variable region to human CD7 of SEQ ID NO: 33 to each other (hzCD7(VH)). Then, both ends of the thus ligated hzCD7(VH) fragment were digested with restriction enzymes EcoRI and ApaI, which were then inserted into the EcoRI-ApaI site of pdCMV-dhfrC-AKA/HzK vector, thereby preparing pdCMV-dhfrC-hzCD7(VH).

All the PCRs during the preparation of such a hzCD7 (VH) fragment were performed with a pre-denaturation at 95° C. for 5 minutes, followed by 30 cycles with Taq DNA polymerase of 94° C., 52° C., and 72° C. for 50 seconds, 50 seconds, and 1 minute, respectively.

<1-2-2> Synthesis of Nucleotide Sequence of Humanized Light Chain Variable Region First, in order to synthesize a signal sequence of a light chain gene having a nucleotide sequence of SEQ ID NO: 48, PCR was performed using pdCMV-dhfr-AKA/HzK (Korean Patent Registration No. 10-0318761) as a template and LHS42 primer represented by SEQ ID NO: 16 and KCleaderback primer represented by SEQ ID NO: 17 in a pair.

Then, in order to synthesize a nucleotide sequence of a light chain variable region of a mouse-derived antibody to human CD7, which has a nucleotide sequence of SEQ ID NO: 49, PCR was performed using scfvCD7-pET21b of example <1-2-1> above as a template and CD7L-F primer represented by SEQ ID NO: 18 and CD7L-R primer represented by SEQ ID NO: 19 in a pair.

In order to humanize the thus obtained light chain variable region of the mouse-derived antibody to human CD7, which has the nucleotide sequence of SEQ ID NO: 49, (1') "humanized light chain variable region fragment 1" having a nucleotide sequence of SEQ ID NO: 50 was obtained by performing PCR using CD7L-F primer represented by SEQ ID NO: 18 and CD7L1-R primer represented by SEQ ID NO: 21; (2') "humanized light chain variable region fragment 2" having a nucleotide sequence of SEQ ID NO: 51 was obtained by performing PCR using CD7L1-F primer represented by SEQ ID NO: 20 and CD7L2-R primer represented by SEQ ID NO: 23; (3') "humanized light chain variable region fragment 3" having a nucleotide sequence of SEQ ID NO: 52 was obtained by performing PCR using CD7L2-F primer represented by SEQ ID NO: 22 and CD7L3-R primer represented by SEQ ID NO: 125; and (4') "humanized heavy chain variable region fragment 4" having a nucleotide sequence of SEQ ID NO: 53 was obtained by performing PCR using CD7L3-F primer represented by SEQ ID NO: 24 and CD7L-R primer represented by SEQ ID NO: 19.

In order to ligate the thus obtained four nucleotide sequence fragments of the humanized light chain variable region to human CD7, recombinant PCR was performed using "humanized light chain variable region fragment 1" and "humanized light chain variable region fragment 2" as templates and CD7H-F primer represented by SEQ ID NO: 18 and CD7L2-R primer represented by SEQ ID NO: 23, thereby obtaining "humanized light chain heavy regions 1-1" having s nucleotide sequence of SEQ ID NO: 54. In addition, recombinant PCR was performed using "humanized light chain variable region fragment 3" and humanized light chain variable region fragment 4" as templates and CD7L2-F primer represented by SEQ ID NO: 22 and CD7L-R primer represented by SEQ ID NO: 19, thereby obtaining "humanized light chain variable region fragments 1-2" having a nucleotide sequence of SEQ ID NO: 55. Then, recombinant PCR was performed using the thus obtained humanized light chain variable region fragments 1-1 and 1-2 as templates and CD7L-F primer represented by SEQ ID NO: 18 and CD7L-R primer represented by SEQ ID NO: 19, thereby preparing a nucleotide sequence of the humanized light chain variable region to human CD7, of SEQ ID NO: 35.

Figure 2:
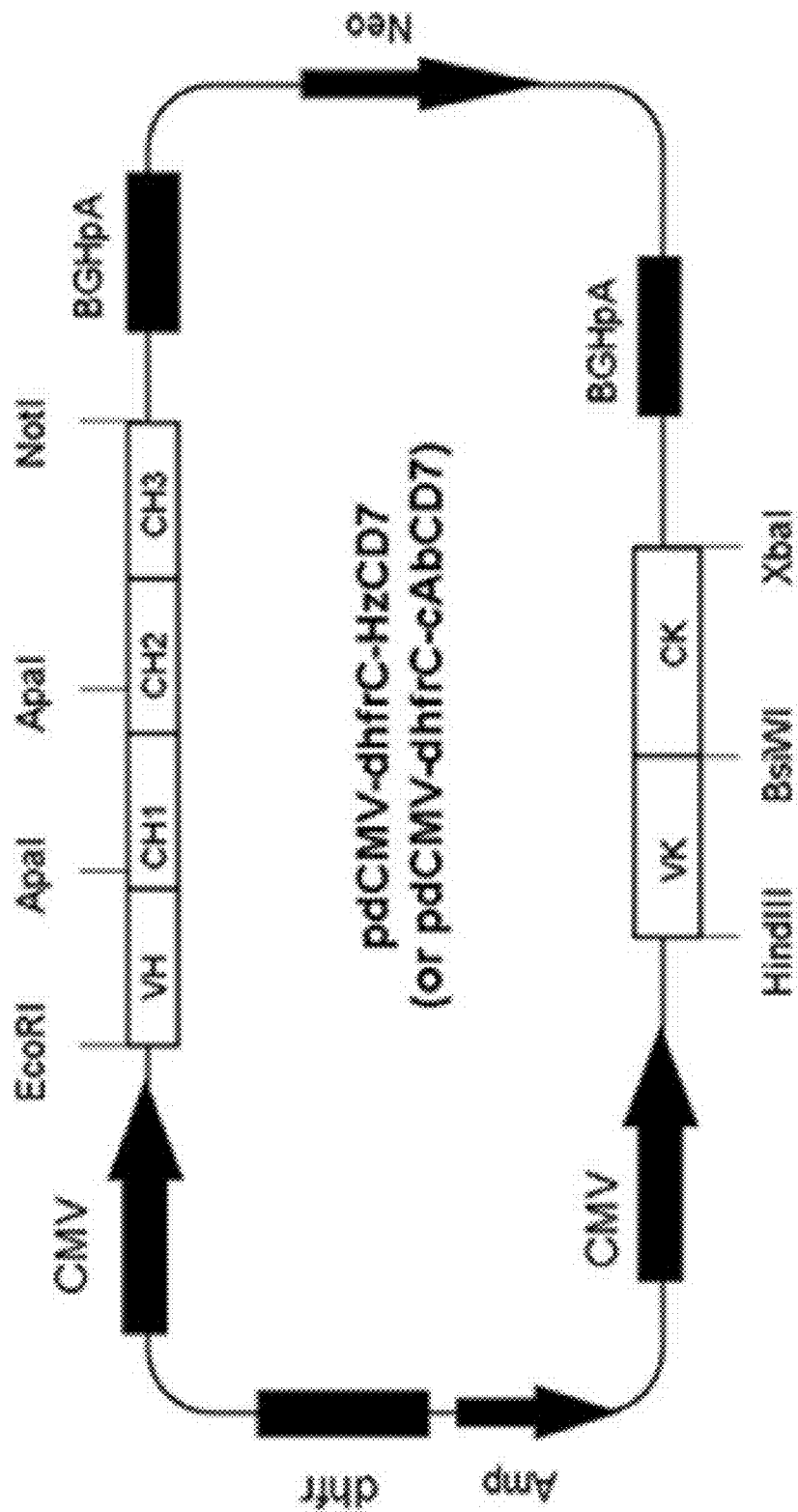
FIG. 2 illustrates a map of pdCMV-dhfrC-HzCD7 vector expressing a heavy chain variable region and a light chain variable region of the humanized antibody of the present invention.

Then, recombinant PCR was performed using the thus obtained signal sequence of SEQ ID NO: 48 and the nucleotide sequence of the humanized light chain variable region to human CD7, of SEQ ID NO: 35, as templates and LHS42 primer represented by SEQ ID NO: 16 and CD7L-R primer represented by SEQ ID NO: 19, to ligate the signal sequence and the nucleotide sequence of the humanized light chain variable region to human CD7, of, SEQ ID NO: 35, to each other (hzCD7(VK). Then, both ends of the thus ligated hzCD7(VH) fragment were digested with restriction enzymes HindIII and BsiWI, which were then inserted into the HindIII-BsiWI site of the pdCMV-dhfrC-hzCD7(VH) prepared in example <1-2-1>, thereby preparing pdCMV-dhfrC-HzCD7 vector having a structure shown in FIG. 2.

All the PCRs during the preparation of such a hzCD7 (VK) fragment were performed with a pre-denaturation at 95° C. for 5 minutes, followed by 30 cycles with Taq DNA polymerase of 94° C., 52° C., and 72° C. for 50 seconds, 50 seconds, and 1 minute, respectively.

<1-3> Nucleotide Sequencing of Prepared Light Chain and Heavy Chain Variable Regions Nucleotide sequencing of the light chain and heavy chain variable regions of pdCMV-dhfrC-hzCD7 clones prepared in example <1-2> was conducted using T7 Sequenase V2.0 DNA sequencing kit (Amersham).

As a result, it was verified that the humanized heavy chain and light chain variable regions to human CD7 are composed of nucleotide sequences of SEQ ID NO: 33 and SEQ ID NO: 35, respectively, as designed in example <1-1>.

<1-4> Construction of Humanized scFv to Human CD7

In order to prepare humanized scFv to human CD7, PCR was performed using the pdCMV-dhfrC-hzCD7 vector prepared in example <1-2> as a template and scFv L-ndeI-F primer represented by SEQ ID NO: 26 and scFv L-R primer represented by SEQ ID NO: 27, thereby obtaining a nucleotide sequence (SEQ ID NO: 35) of the light chain variable region of the humanized antibody to human CD7. PCR was performed using the pdCMV-dhfrC-hzCD7 vector as a template and scFv H-F primer represented by SEQ ID NO: 30 and scfv H-XhoI-R primer represented by SEQ ID NO: 31, thereby obtaining a nucleotide sequence (SEQ ID NO: 33) of the heavy chain variable region of the humanized antibody to human CD7. Last, PCR was performed using scfvCD7-pET21b as a template and linker-F primer represented by SEQ ID NO: 28 and linker-R primer represented by SEQ ID NO: 29, thereby obtaining a nucleotide sequence of SEQ ID NO: 56 coding the linker of scFv.

Figure 3:
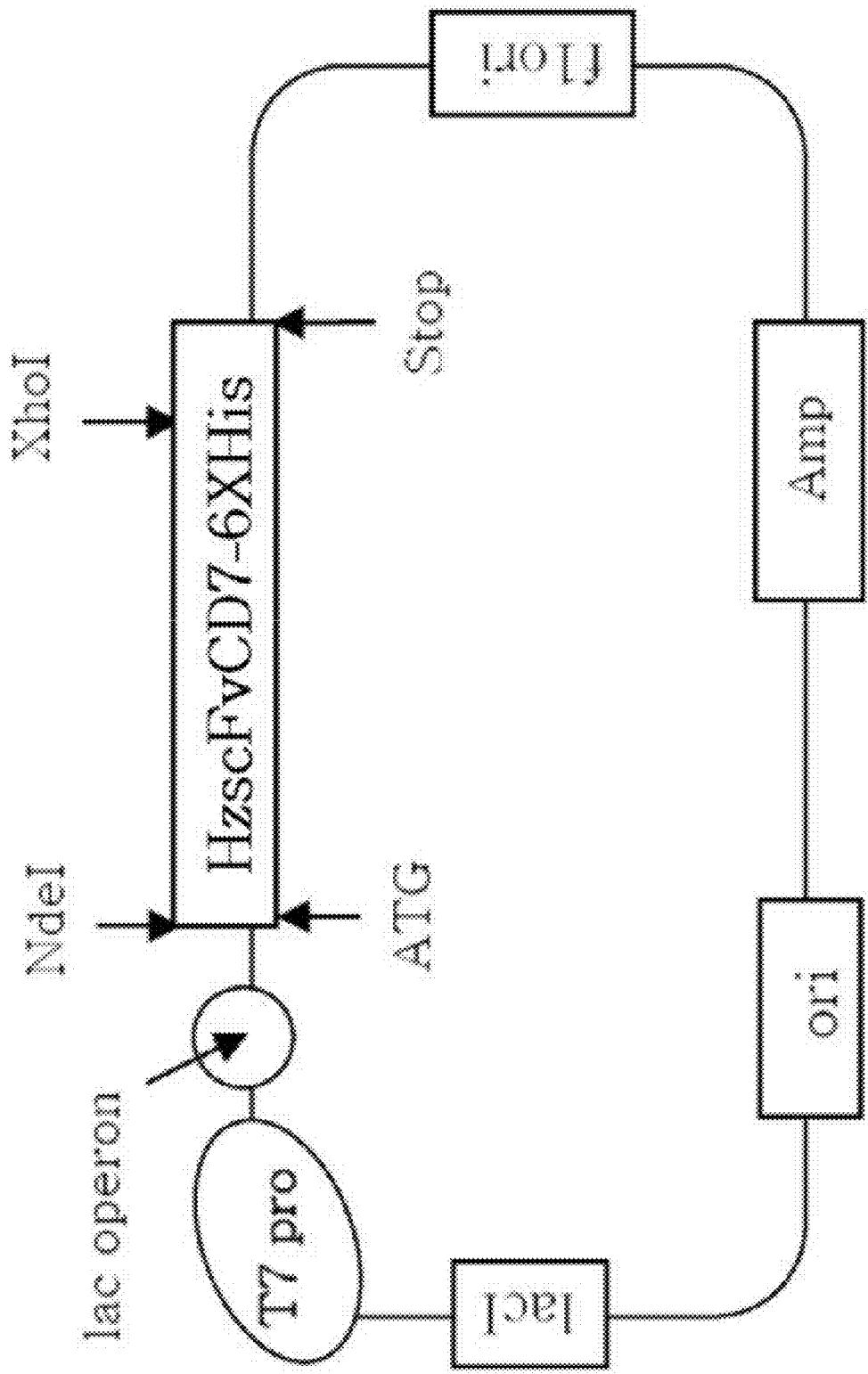
FIG. 3 illustrates a map of HzscfvCD7-pET21b expression vector expressing HzscFvCD7 of the present invention.

As described above, recombinant PCR was performed using the thus obtained light chain variable region, linker region, and heavy chain variable region as templates and scFv L-ndeI-F primer represented by SEQ ID NO: 26 and scfv H-XhoI-R primer represented by SEQ ID NO: 31, to sequentially ligate the light chain variable region, linker region, and heavy chain variable region to each other (hzscFvCD7). Then, both ends of the hzscFvCD7 fragment ligated as above were digested with restriction enzymes ndeI and XhoI, which were then inserted into the ndeI-XhoI site of the scfvCD7-pET21b vector, thereby preparing HzscfvCD7-pET21b expression vector having a structure shown in FIG. 3.

All the PCRs during the preparation of the hzscFvCD7 fragment above were performed with a pre-denaturation at 95° C. for 5 minutes, followed by 30 cycles with Taq DNA polymerase of 94° C., 52° C., and 72° C. for 50 seconds, 50 seconds, and 1 minute, respectively.

<1-5> Nucleotide Sequencing of Prepared Humanized scFv to Human CD7 (HzscFvCD7)

Nucleotide sequencing of HzscFvCD7 of the clones prepared in example <1-4> was conducted using T7 Sequenase V2.0 DNA sequencing kit (Amersham).

As a result, it was verified that the light chain and heavy chain variable regions of HzscFvCD7 were derived from nucleotide sequences (SEQ ID NO: 33 and 35) of the light chain (HzCD7(VK)) and heavy chain (HzCD7(VH)) variable regions of pdCMV-dhfrC-HzCD7.

EXAMPLE 2

Expression and Purification of humanized scFv to Human CD7 (HzscFvCD7)

*E. coli* strain BL21 was transformed with the HzscfvCD7-pET21b constructed in example <1-4> to obtain BL21 single colony. The BL21 single colony was inoculated in LB liquid media containing ampicillin, and then cultured in a shaking incubator at 37° C. The absorbance thereof was measured at O.D. 600 nm using a spectrophotometer, and the BL21 single colony was cultured until the O.D. value reached 0.6 to 0.8, followed by the addition of IPTG, and then cultured at 26° C. overnight. The bacteria pellets obtained by 4000×g centrifugation at 4° C. for 10 minutes were sonicated using a sonicator while the lysis buffer was added thereto, and again centrifuged at 4000×g for 40 minutes at 4° C. to separate a supernatant. After that, humanized scFv to human CD7 (HzscFvCD7) was purified using FPLC.

The purified HzscFvCD7 was subjected to dialysis in DPBS of pH 7.4, and then concentrated using a concentration column. The purified HzscFvCD7 was subjected to a concentration measurement using BCA kit (Pierce, US) and then a size measurement through SDS-PAGE.

As a result, the purified HzscFvCD7 was verified to have a size of about 27 kDa (FIG. 4).

EXAMPLE 3

Preparation of carrier using specificity of HzscFvCD7

<3-1> Conjugation of HzscFvCD7 and Poly Oligo-9-Arginine

As one method for using HzscFvCD7 as a carrier for siRNA, poly oligo-9-Arginine (hereinafter, referred to as 9R) capable of binding to siRNA was conjugated to HzscFvCD7.

More specifically, the N-terminal of HzscFvCD7 was inactivated with sulfo-NHS-acetate, and then unreacted sulfo-NHS-acetate was removed using the dialysis membrane. Then, the primary amine group (N-terminal) of 9R was disulfide-bonded to Cys of the C-terminal of HzscFvCD7 through the NHS-EDC reaction, thereby preparing a carrier for siRNA having a structure shown in FIG. 5(A).

Then, it was confirmed through MALDI-TOF whether HzscFvCD7 bound to 9R. As a result, it was verified that HzscFvCD7 chemically bound to 9R by about 90% or more (FIG. 5(B)).

<3-2> Conjugation of HzscFvCD7 and Liposome

The liposome was prepared to have the following composition, and then used to deliver siRNA.

HSPC:HSPE:Chol:DCchol:DSPE-PEG-Mal=6:1:1:1: 0.14

Figure 6:
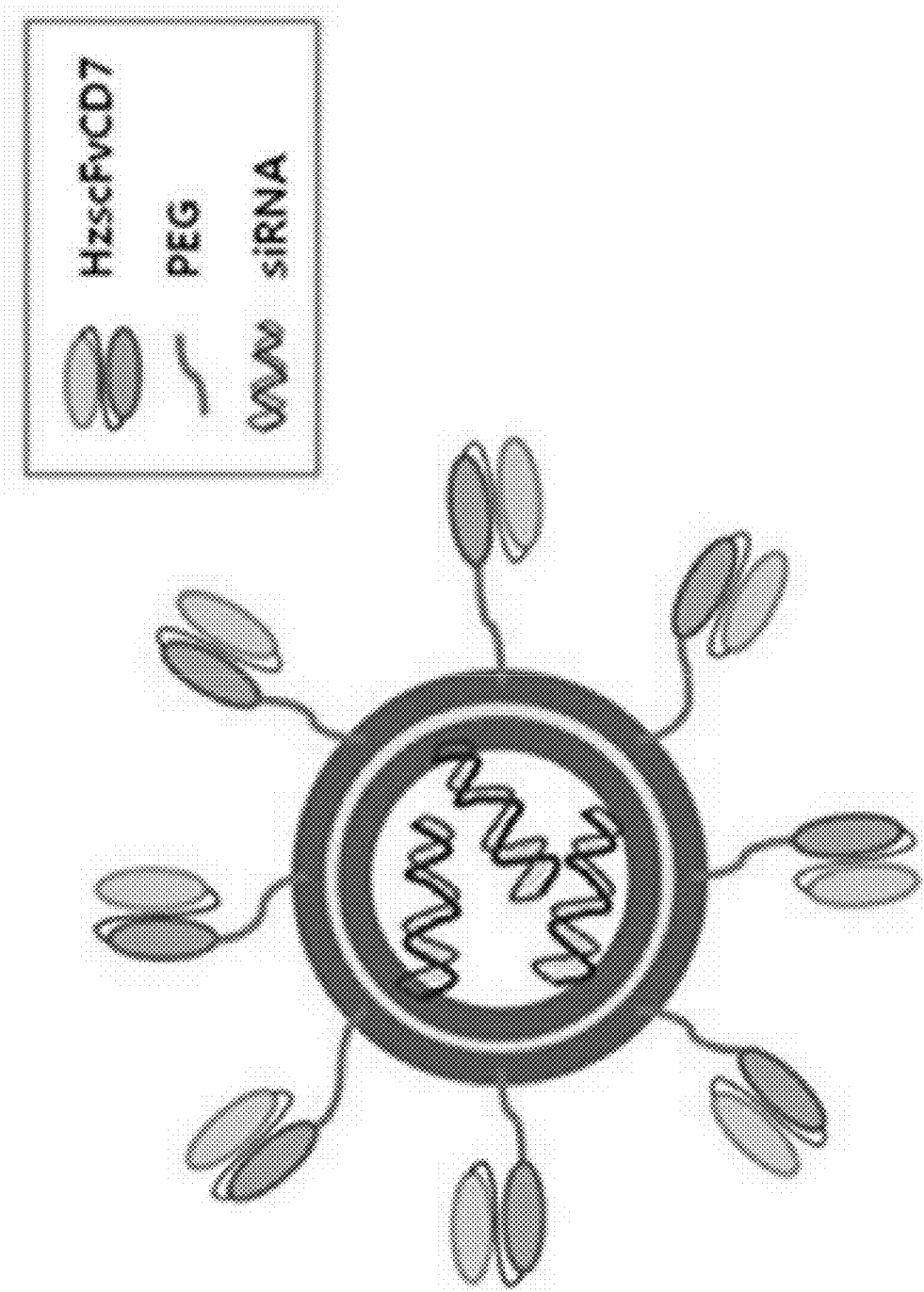
FIG. 6 is a schematic view showing a structure of a complex in which HzscFvCD7 binds to liposome.
Figure 7A:
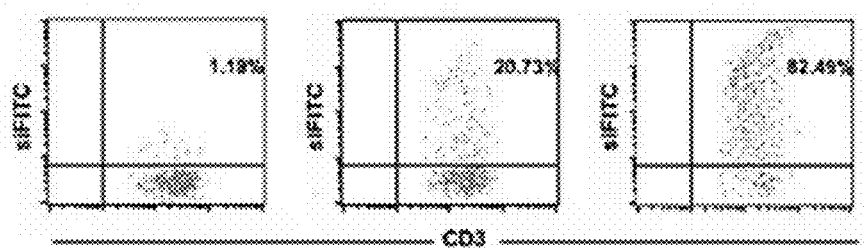
FIG. 7(A) shows graphs illustrating results confirming induction efficiency of HzscFvCD7-9R/siFITC complex into Jurkat cells.
Figure 7B:
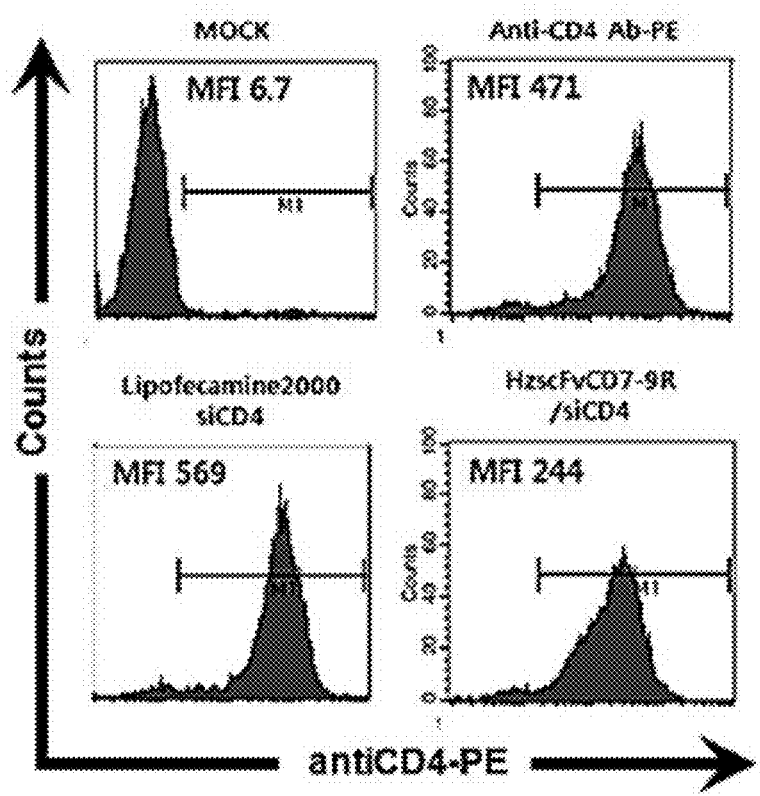
FIG. 7(B) shows graphs illustrating results that CD4 expression is silenced by HzscFvCD7-9R/siCD4 complex in Jurkat cells.
Figure 8:
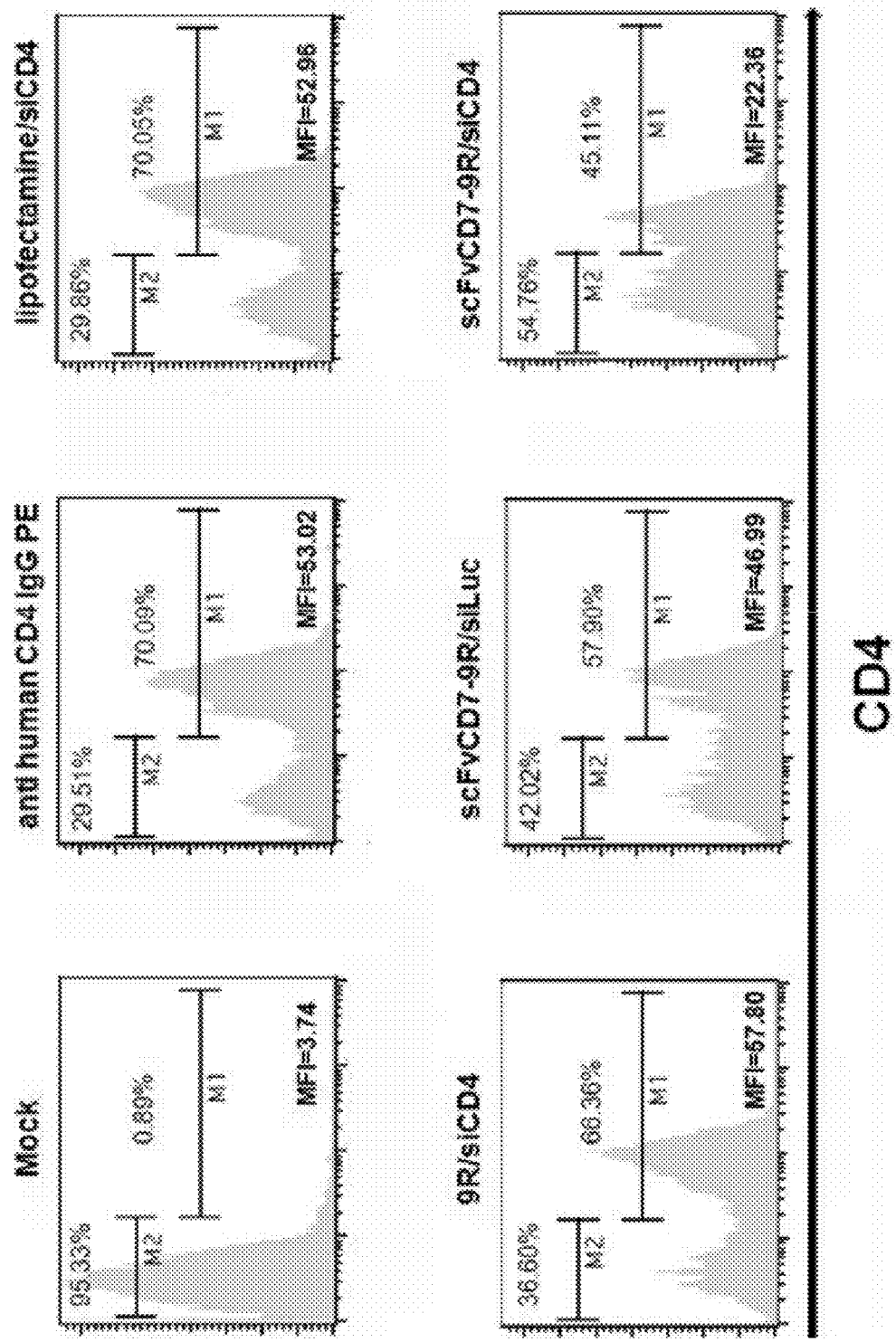
FIG. 8 shows graphs illustrating results that CD4 expression was silenced by HzscFvCD7-9R/siCD4 complex in peripheral blood mononuclear cells (PBMCs).
Figure 9:
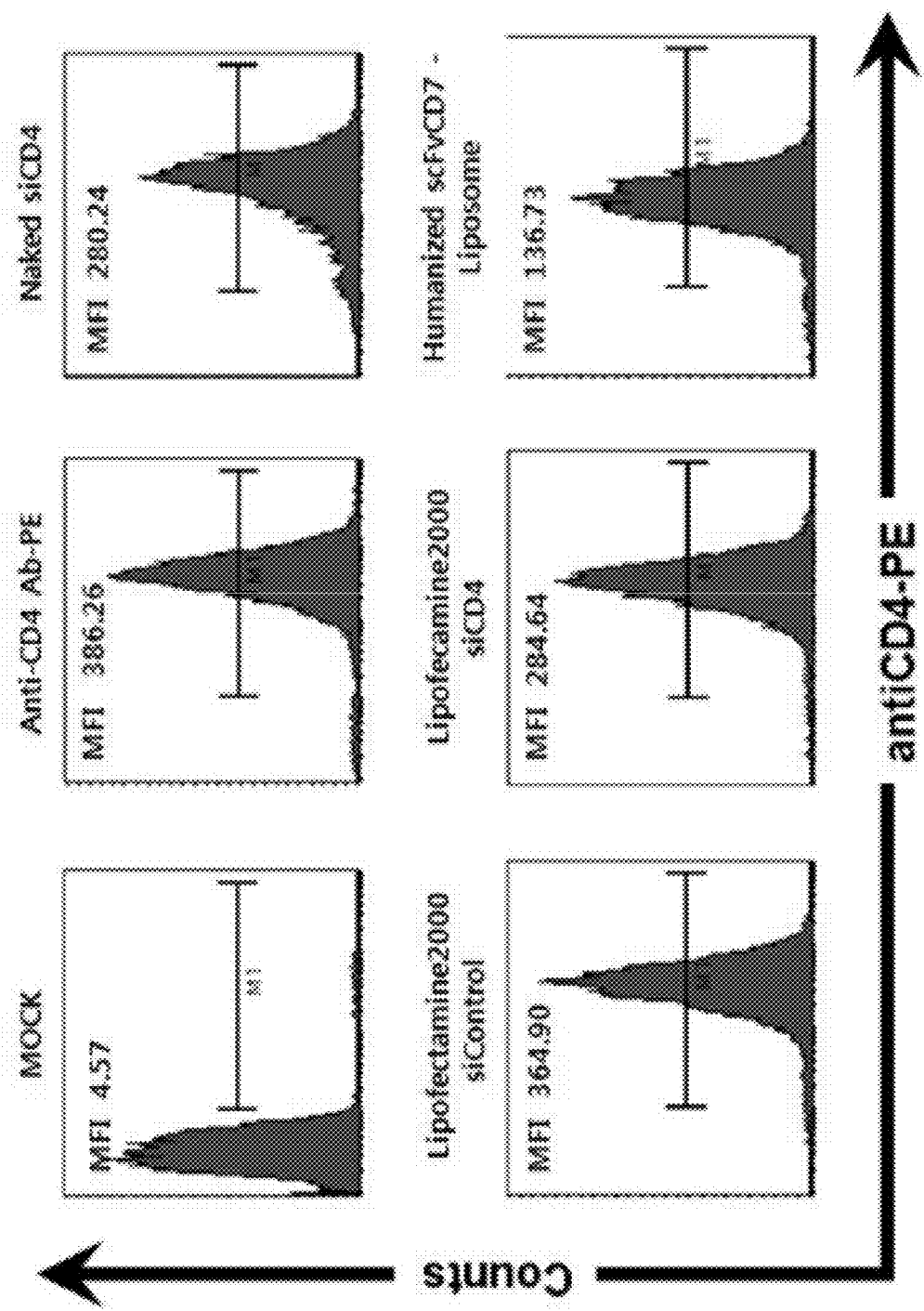
FIG. 9 shows graphs illustrating results that CD4 expression was silenced by HzscFvCD7-liposome/siCD4 complex in Jurkat cells.
Figure 10:
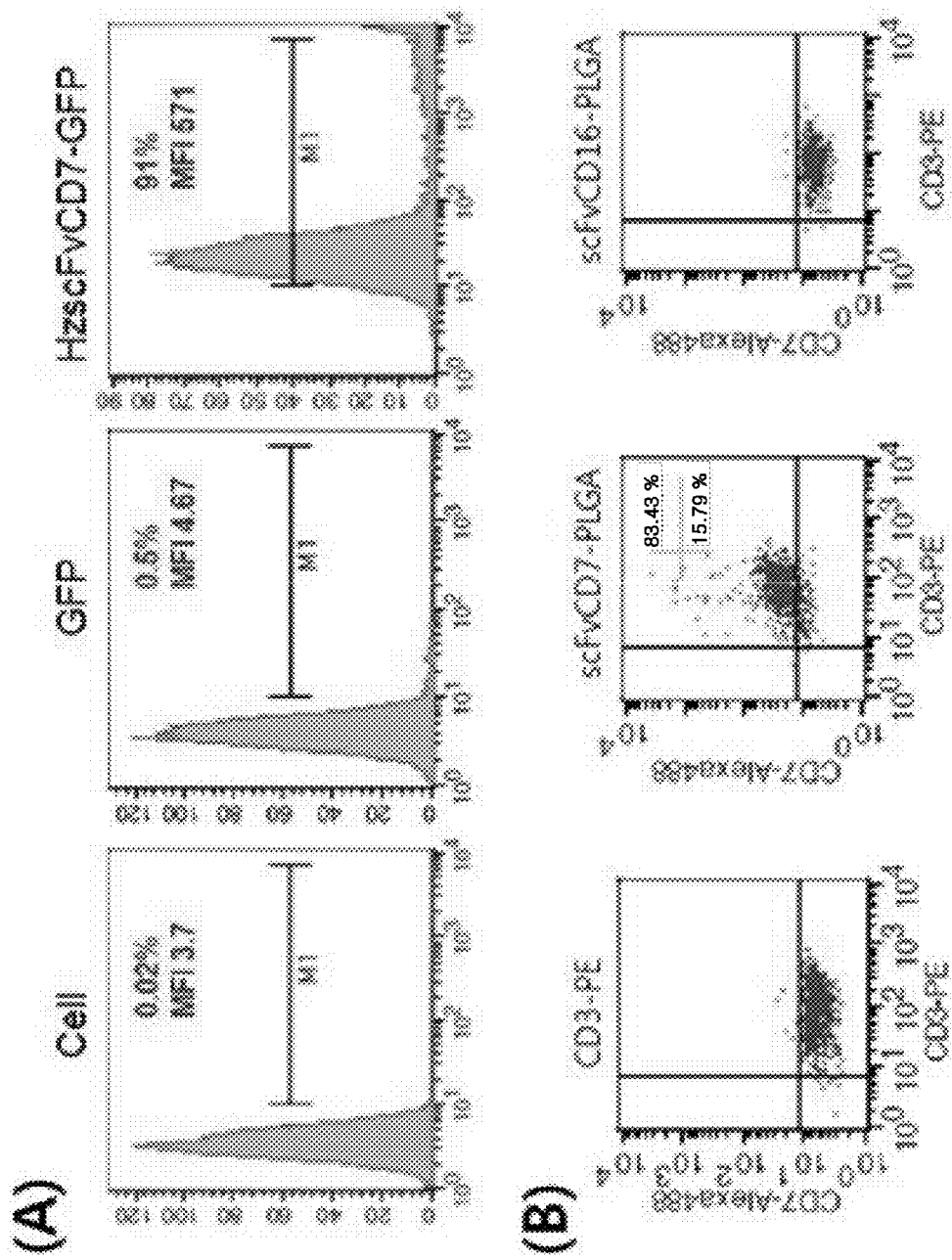
FIG. 10(A) shows graphs illustrating results that GFP was introduced into HSB2 cells by HzscFvCD7-GFP complex.
FIG. 10(B) shows graphs illustrating results that PLGA was introduced into Jurkat cells by HzscFvCD7-PLGA complex.
Figure 11:
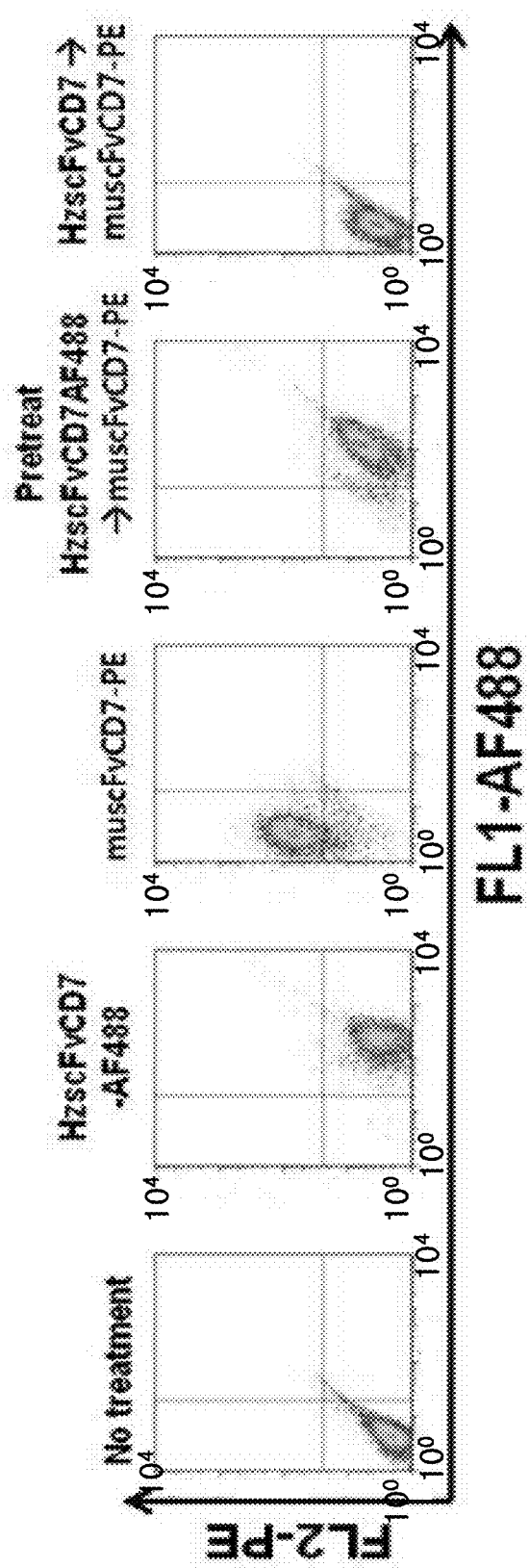
FIG. 11 shows graphs illustrating competition assay results of HzscFvCD7 and muscFvCD7.

Lipid was dissolved in chloroform in the 5-ml flask, and a dry film was prepared using a rotary evaporator, followed by removal of remaining chloroform using a desiccator. The reaction product of 9-Arginine and siRNA (molar ratio=5:1), which was obtained by previously performing the reaction in PBS, was put on the lipid dry film, followed by hydration, and then extrusion was performed using a PC membrane (100 nm). The thus prepared liposome was put in a 1.5-ml tube, and HzscFvCD7 and DSPE-PEG-Mal were mixed at a molar ratio of 1:1. The mixture was allowed to react (Maleimid reaction, 25° C., pH 7.4), followed by vortexing for 2 hours, and then subjected to ultracentrifugation at 80000×g for 40 minutes at 4° C. to remove unbound humanized HzscFvCD7, thereby preparing a carrier for siRNA having a structure of FIG. 6.

EXAMPLE 4

Evaluation on In Vitro Efficacy of HzscFvCD7 as Carrier

In order to evaluate targeting efficacy of HzscFvCD7 as a carrier, siRNA (hereinafter, referred to as siCD4) inhibiting the CD4 expression on T cell surfaces, FITC-conjugated siCD4 (hereinafter, referred to as siFITC), green fluorescent protein (GFP), or poly(lactic-co-glycolic acid) (PLGA) polymer was allowed to chemically bind to a carrier including HzscFvCD7, and a Jurkat cell line and a primary cell line of peripheral blood mononuclear cells (PBMCs) were treated with the resultant material.

<4-1> Evaluation on siRNA Delivery Efficacy to T Cells or Jurkat Cells Using "HzscFvCD7-9R"

First, the siFITC was mixed with the HzscFvCD7-9R prepared in example <3-1> to prepare a complex, and then Jurkat cells were treated with the complex. The induction efficiency of siFITC into Jurkat cells and the inhibition rate of CD4 expression were analyzed using a flow cytometry instrument.

As a result, it was verified that 80% or more of siFITC was introduced into the Jurkat cells (FIG. 7(A)), and the CD expression was silenced by about 50% in the Jurkat cells (FIG. 7(B)). It can be seen from the above results that the HzscFvCD7-9R can introduce siRNA into T cells, the HzscFvCD7-18R6L delivers siRNA specifically to T cells and silences the CD4 expression.

Then, siCD4 was mixed with the HzscFvCD7-9R prepared in example <3-1> to prepare a complex, and then peripheral blood mononuclear cells were treated with the complex. The expression rate of CD4 was analyzed using a flow cytometry instrument.

As a result, the CD expression was silenced by 50% or more in the peripheral blood mononuclear cells (FIG. 8). It can be seen from the above results that the HzscFvCD7-18R6L delivers siRNA specifically to T cells and silences the CD4 expression.

<4-2> Evaluation on siRNA Delivery Efficacy to T Cells Using "HzscFvCD7-Liposome"

In order to evaluate targeting efficacy of HzscFvCD7-liposome to T cells, siCD4 was mixed with the HzscFvCD7-liposome prepared in example <3-2>, and then Jurkat cells were treated with the mixture. The inhibition rate of CD4 expression was analyzed using a flow cytometry instrument.

As a result, the CD expression was silenced by about 65% in T cells (FIG. 9). It can be seen from the above results that the HzscFvCD7-liposome delivers siRNA specifically to T cells and silences the CD4 expression.

<4-3> Evaluation on Protein or Polymer Delivery Efficacy to T Cells Using "HzscFvCD7"

In order to evaluate targeting efficacy of HzscFvCD7 to T cells, GFP protein or PLGA was chemically conjugated with the HzscFvCD7 prepared in example 2 by the same method as shown in example <3-1> for 9R binding, and then HSB2 cells and Jurkat cells were treated with the conjugate. The GFP or PLGA delivery degree to T cells was analyzed using a flow cytometry instrument.

As a result, it was verified that the induction efficiency of GFP protein to T cells (HSB2 cells) was 90% or more (HSB2 cells) (FIG. 10(A)), and the induction efficiency of PLGA to T cells (Jurkat cells) was also 80% or more (FIG. 10(B)). It can be seen from the above results that the HzscFvCD7 can deliver protein or polymer as well as siRNA specifically to T cells.

EXAMPLE 5

Characterization of HzscFvCD7

<5-1> Confirmation on Whether HzscFvCD7 and Mouse-Derived scFv to Human CD7 Recognize Same Antigen Competition assay was performed in order to verify whether the HzscFvCD7 prepared in example 2 and the existing mouse-derived scFv to human CD7 (muscFvCD7 (Kumar et al., Cell, 2008 Aug. 22; 134(4):577-586)) recognize the same antigen. First, Jurkat cells were treated with HzscFvCD7 bound with Alexa 488 to confirm the binding of HzscFvCD7 to Jurkat cells as T cells. Then, Jurkat cells were cross-treated with HzscFvCD7 and T3Ale (full-length antibody including muscFvCD7 (Kumar et al., Cell, 2008 Aug. 22; 134(4):577-586)) to confirm the binding to Jurkat cells.

As a result, it was verified that the binding of muscFvCD7 to Jurkat cells were inhibited when Jurkat cells were treated with HzscFvCD7 before muscFvCD7 (FIG. 11). It can be seen from the above results that HzscFvCD7 and muscFvCD7 recognize the same antigen.

<5-2> Evaluation on T-Cell Targeting Efficacy of HzscFvCD7 in Humanized Mouse

<5-2-1> Evaluation on T-Cell Targeting Efficacy of HzscFvCD7 in Humanized Mouse Hu-HSC In order to evaluate T-cell targeting efficacy of HzscFvCD7 prepared in example 2 in vivo, the following experiments were conducted.

First, humanized mouse Hu-HSC was prepared according to Ishikawa et al. (Blood 2005; 106:1565-1573) and Kumar et al. (Cell, 2008 Aug. 22; 134(4):577-586), and the presence of human cells in blood, liver, thymus, and brain of the mouse Hu-HSC after 8 weeks was confirmed using a flow cytometry instrument.

Figure 12:
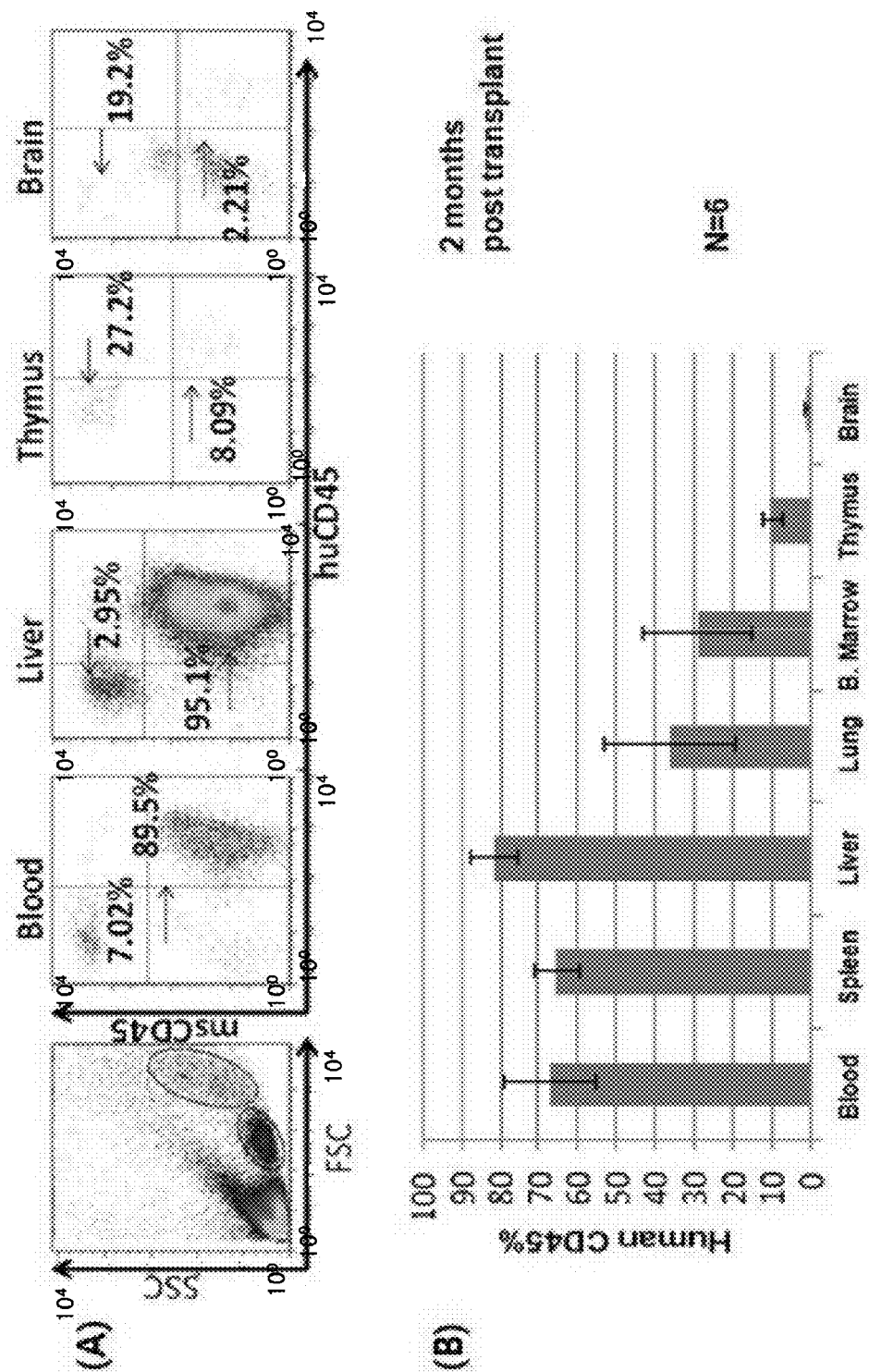
FIG. 12 shows graphs confirming whether human cells are present in tissues of humanized mouse (Hu-HSC).
Figure 13:
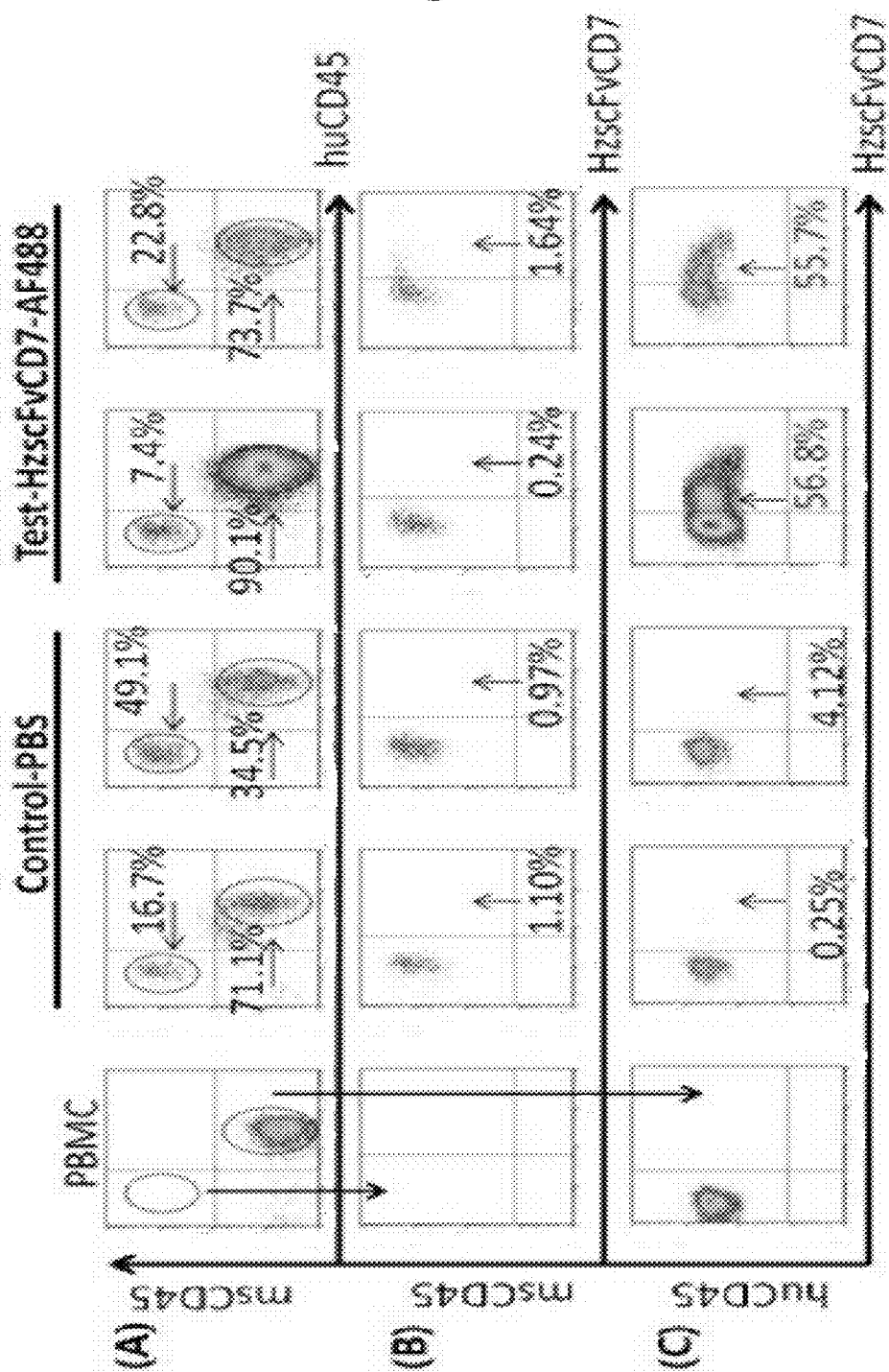
FIG. 13 illustrates results confirming specificity of HzscFvCD7 to human cells in humanized mouse (Hu-HSC).

As a result, it was verified that 70% of cells were differentiated into human cells after about 8 weeks, and a large amount of human leukocytes were present in pancreas and liver, including blood (FIG. 12), and, especially, it was verified that a large amount of human leukocytes were also present in peripheral blood mononuclear cells (PBMCs) of Hu-HSC (FIG. 13(A)).

Next, HzscFvCD7 bound with Alexa 488 was intravenously injected into mouse Hu-HSC one time to collect peripheral blood mononuclear cells (PBMCs), and it was confirmed using a flow cytometry instrument whether HzscFvCD7 was delivered to CD45+ human cells, and delivered to CD3+ T cells of human cells.

Figure 14:
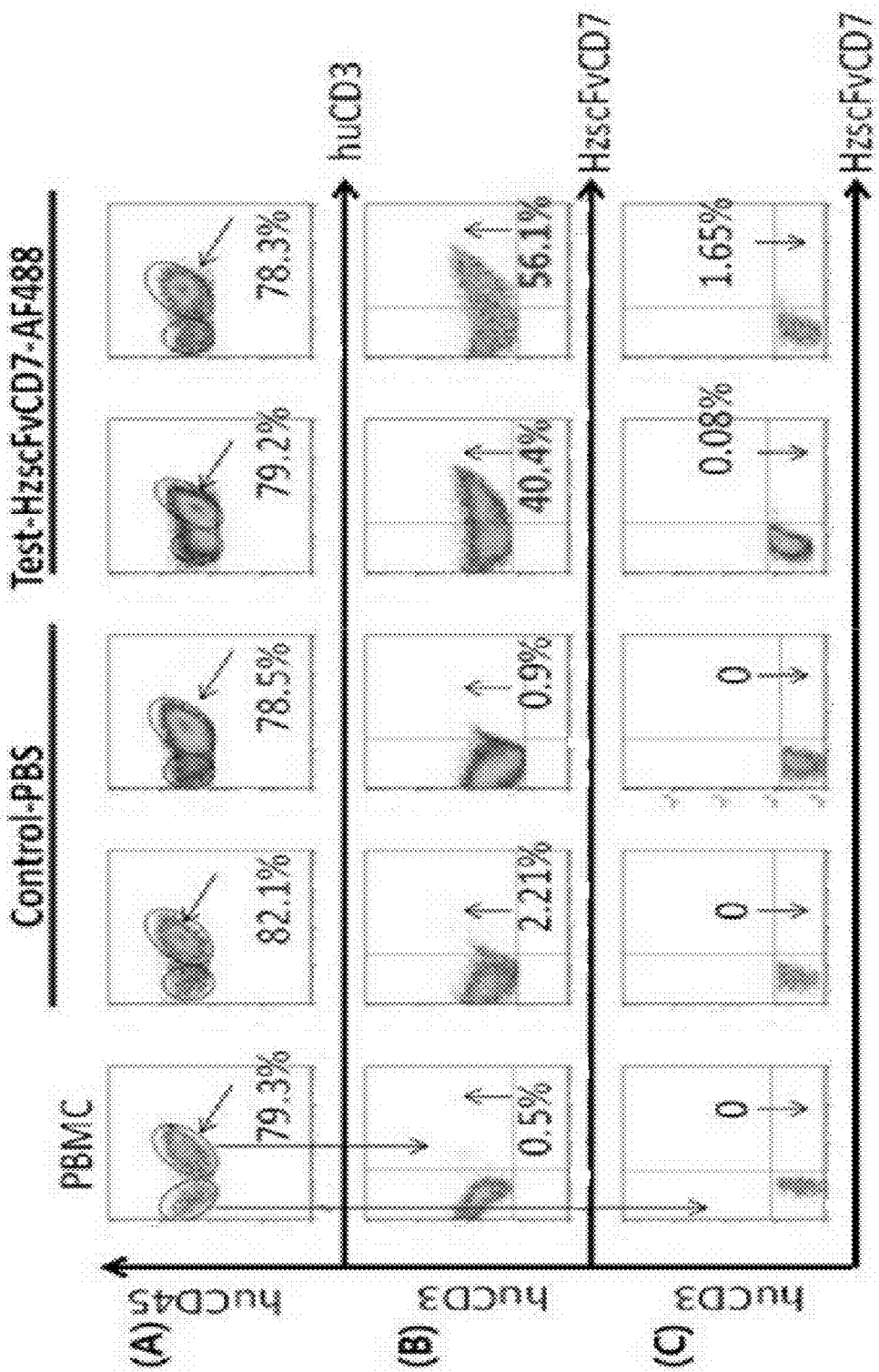
FIG. 14 illustrates results confirming specificity of HzscFvCD7 to human T cells of human cells in humanized mouse (Hu-HSC).

As a result, it was verified that HzscFvCD7 never bound to the mouse cells (FIG. 13(B)), but about 50% of HzscFvCD7 bound to CD45+ human cells through a single intravenous injection (FIG. 13(C)). In addition, it was verified that about 80% of the CD45+ human cells were CD3+ T cells (FIG. 14(A)), and HzscFvCD7 specifically bound to about 40% to 60% of CD3+ T cells (FIG. 14(B)). Furthermore, it was verified that HzscFvCD7 did not bind to CD3− cells without CD3 expression, in CD45+ human cells (FIG. 14(C)). From the above results that HzscFvCD7 can target about 40% to 60% of T cells through only a single intravenous injection, the possibility of targeting most of T cells by repetitive administration of HzscFvCD7 was verified.

<5-2-2> Evaluation on T-Cell Targeting Efficacy of HzscFvCD7 in Humanized Mouse Hu-PBL Humanized mouse Hu-PBL was prepared according to Nakata et al. (J Virol 2005; 79:2087-2096) and Kumar et al. (Cell, 2008 Aug. 22; 134(4):577-586).

The complex of HzscFvCD7-9R and siFITC prepared in example <4-1> or the complex of HzscFvCD7 and PLGA prepared in example <4-3> was intravenously injected into mouse Hu-PBL one time to collect blood, and it was confirmed using a flow cytometry instrument whether siFITC or PLGA was delivered to T cells.

Figure 15:
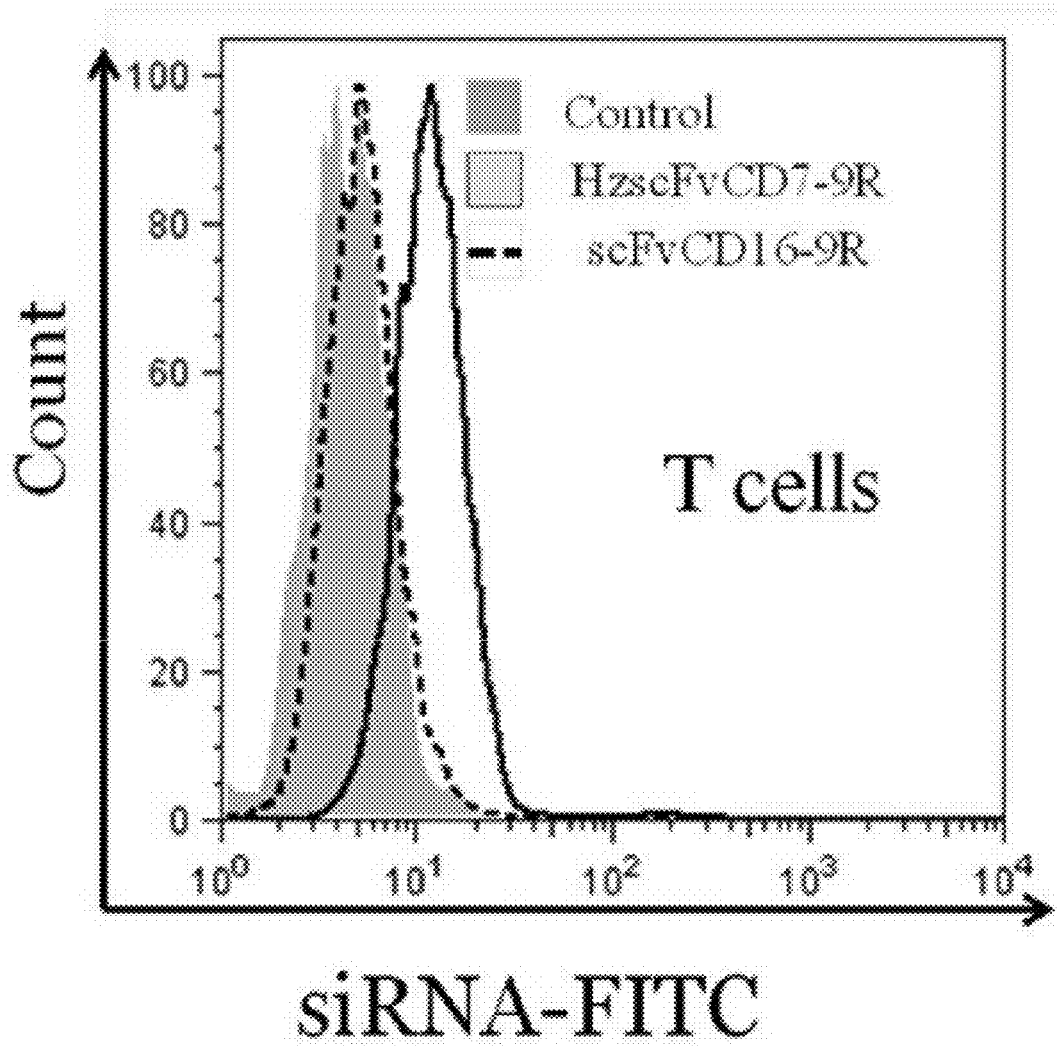
FIG. 15 is a graph illustrating results confirming whether siFITC was specifically delivered to T cells by HzscFvCD7-9R/siFITC complex in humanized mouse (Hu-PBL).
Figure 16:
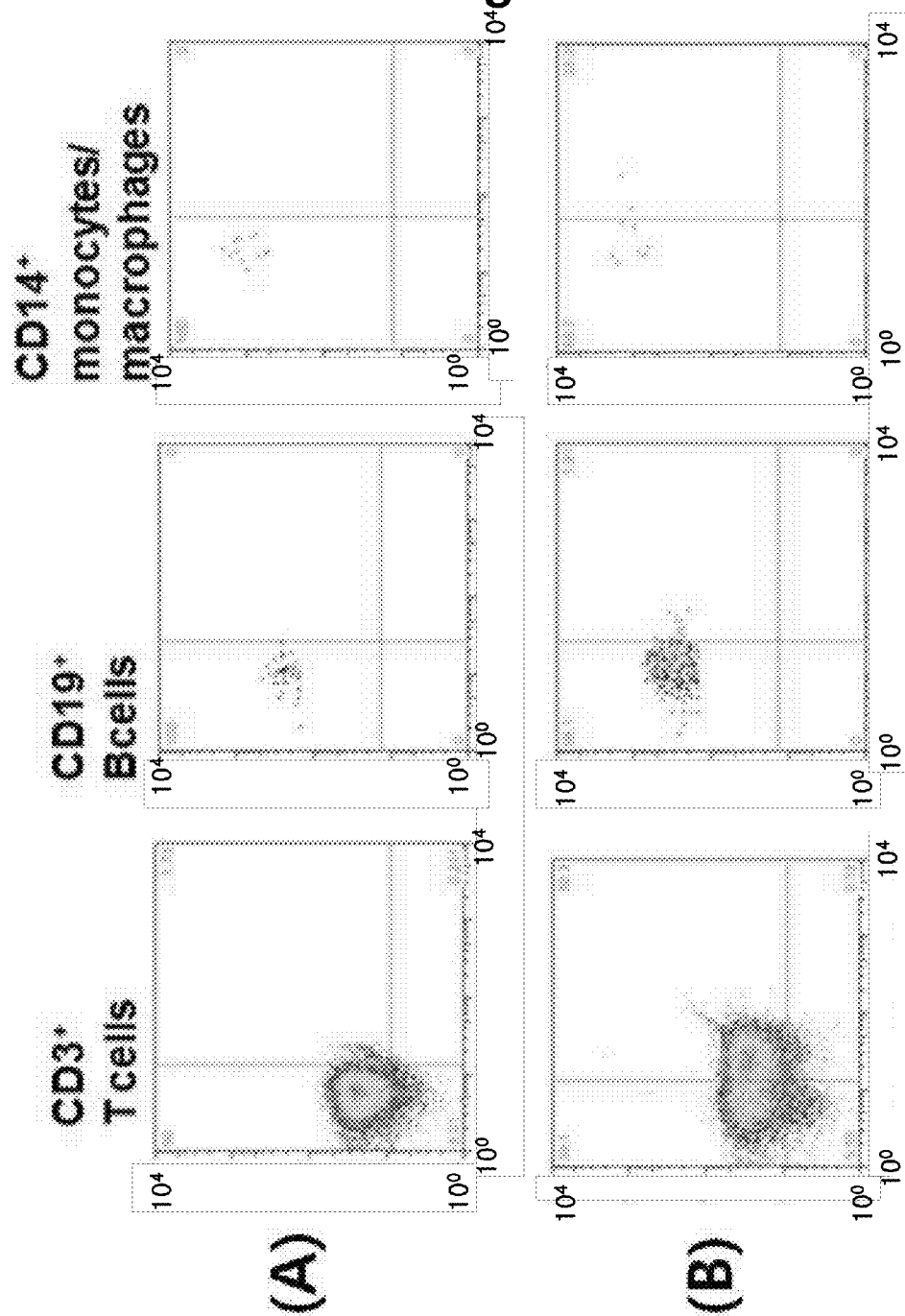
FIGS. 16(A) and 16(B) show graphs illustrating results confirming whether PLGA NP conjugated to huscFvCD7 was specifically delivered to mouse CD45+ T cells (FIG. 16A) and human CD45+ T cells (FIG. 16B) by different human leukocyte subtypes (CD3, CD19, CD14) of humanized mouse (Hu-PBL).

As a result, it was verified that HzscFvCD7-9R delivered siFITC specifically to human T cells (FIG. 15), and delivered PLGA specifically to human T cells (FIG. 16).

<5-3> Confirmation on Pharmacokinetics (PK) of HzscFvCD7 in Humanized Mouse

HzscFvCD7 bound with Alexa 488 (HzscFvCD7-AF488) was intravenously injected into the tail of mouse Hu-HSC to collect blood after 5, 30, 60, 120, 140, and 900 minutes, and then the presence of AF488 was confirmed using PKSolver.

Figure 17:
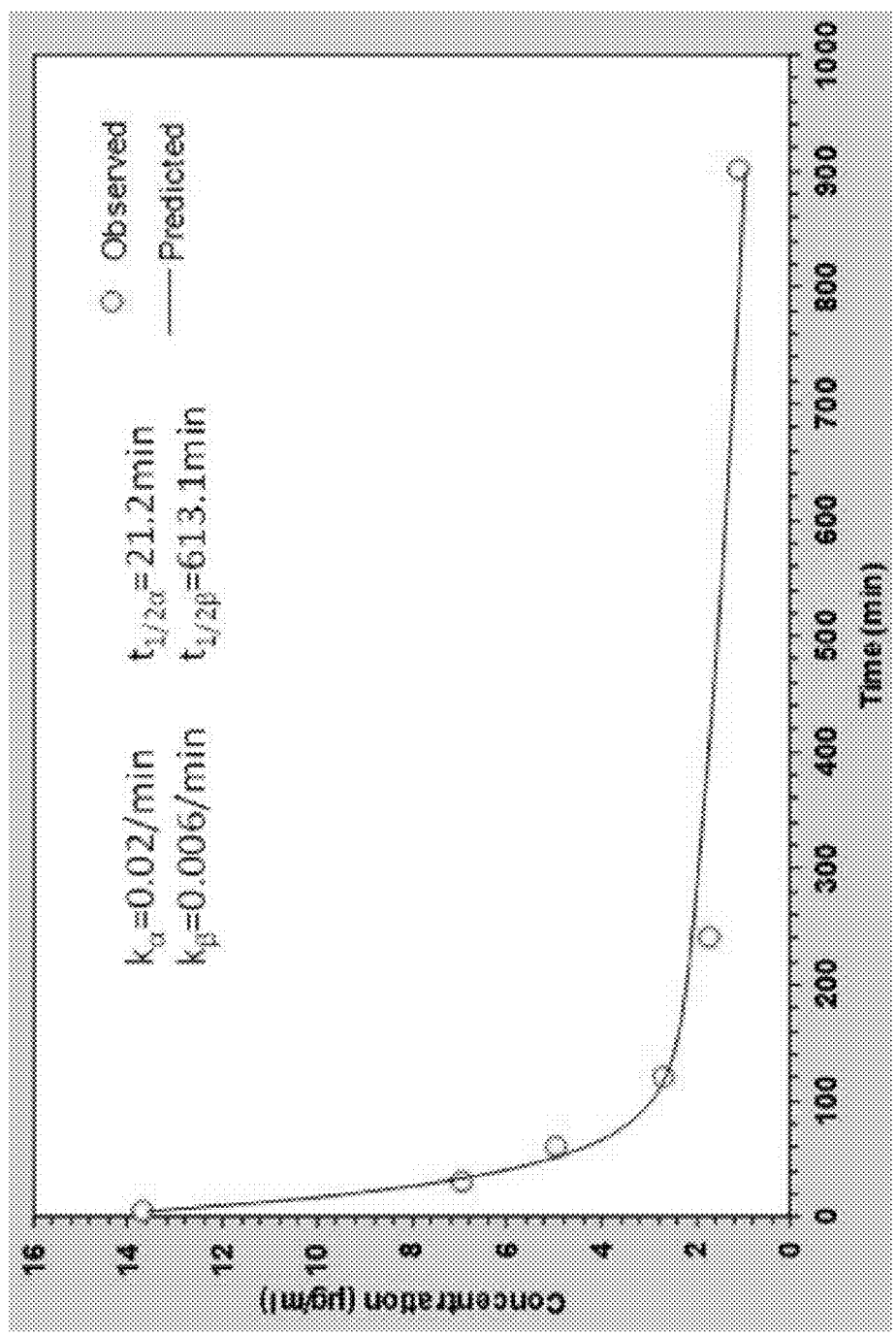
FIG. 17 is a graph illustrating pharmacokinetics (PK) assay in humanized mouse (Hu-PBL).

As a result, it was measured that the delivery half-life of HzscFvCD7 as a carrier was about 21 minutes, and the HzscFvCD7 was completely degraded after 10 hours (FIG. 17). It can be seen from the above results that the HzscFvCD7 of the present invention has an excellent PK value compared with the existing developed humanized antibody (table 1).

TABLE 1

Comparision of PK value between HzscFvCD7 and previously developed humanized antibody/scFv

| scFv | PK (pharmacokinetics) | Reference |
|---|---|---|
| HzscFvCD7 | $T_{1/2\alpha}$ = 21.2 min<br>$T_{1/2\beta}$ = 1.3 h | — |
| Hu-scFv3077<br>(anti GM-CSF) | $T_{1/2\alpha}$ = 7.12 min<br>$T_{1/2\beta}$ = 2 h | Krinner et al., Protein Eng Des Sel. 2006 Oct; 19(10):461-70 |
| ML7-wt<br>(anti CD22) | $T_{1/2\alpha}$ = 36 min<br>$T_{1/2\beta}$ = — | Arndt et al., Int J cancer. 2003 Dec 10;107(5):822-9 |
| G28-5 scFv-PE40<br>(anti CD40 immunotoxin) | $T_{1/2\alpha}$ = 16.7 min<br>$T_{1/2\beta}$ = 45.3 mm | Francisco et al, Blood. 1997 Jun 15;89(12):4493-500 |
| hu/muCC49 scFv<br>(anti TAG72) | $T_{1/2\alpha}$ = 6 min<br>$T_{1/2\beta}$ = — | Pavlinkova et al., Cancer Immunol Immunother. 2000 Jul;49(4-5):267-75 |

EXAMPLE 6

Confirmation on Humanization of HzscFvCD7

<6-1> Measurement of Immune Response of HzscFvCD7 Using Human Anti-Mouse Serum (HAMA)

Purified mAbCD7, muscFvCD7 (Kumar et al., Cell, 2008 Aug. 22; 134(4):577-586), and HzscFvCD7 prepared in example 2 were titrated to 10 ug/ml, and respectively dispensed on the ELISA plate, followed by HAMA treatment, to confirm the immune response. HRP-conjugated goat anti-human Fc specific mAb was used as a secondary antibody of HAMA.

Figure 18:
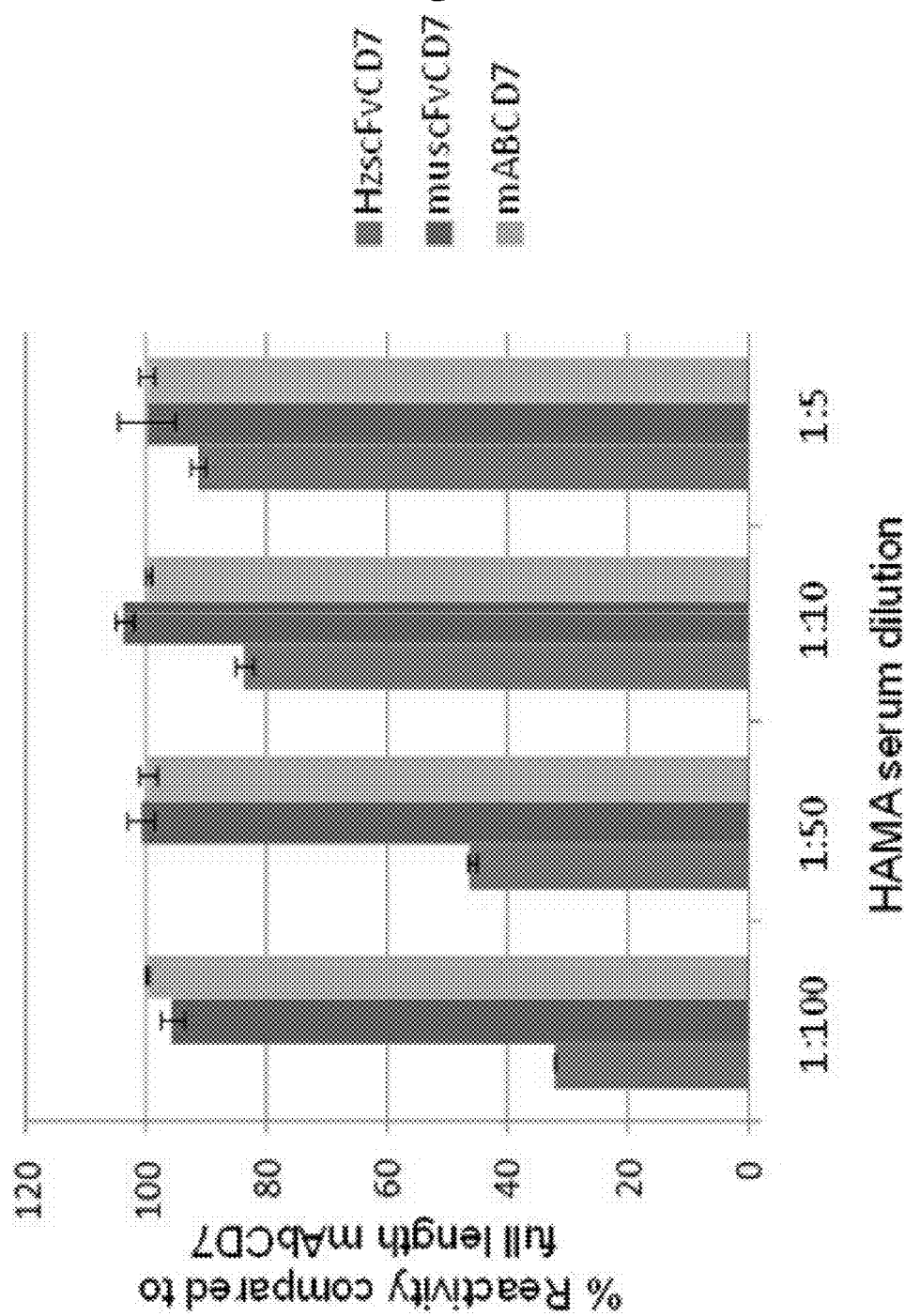
FIG. 18 is a graph illustrating in vitro measurement results of antigenicity of HzscFvCD7 in human body by using human-anti-mouse antibody.

As a result, it was verified that, as for the HzscFvCD7 of the present invention, the immune response by the HAMA gradually decreased as the HAMA was diluted, and the immune response decreased by approximately 70% when the HAMA was diluted at 1:100 (see FIG. 18). It can be seen from the above results that HzscFvCD7 hardly causes the immune response by the human antibody in vitro.

<6-2> Measurement of Immune Response of HzscFvCD7 in Humanized Mouse

The Hu-BLT mouse model (Shimizu et al. (Blood, 2010; 115:1534-1544) and Melkus et al. (Nat Med. 2006; 12(11): 1316-1322)) was divided into (1) "HzscFvCD7 treatment group" and (2) "DNP-KLH (2,4-dinitrophenylated keyhole limpet protein) treatment group", and 200 ug of HzscFvCD7 and 100 ug of DNP-KLH as antigens were injected thereinto. After 2 weeks, the equivalent amount of antigens (200 ug of HzscFvCD7 and 100 ug of DNP-KLH) were secondarily injected into the respective antigen treatment groups, and then pancreatic cells were isolated. The isolated pancreatic cells were stained with carboxyfluorescein succinimidyl ester (CFSE), and treated with the same antigen to induce differentiation and proliferation of pancreatic cells.

Figure 19:
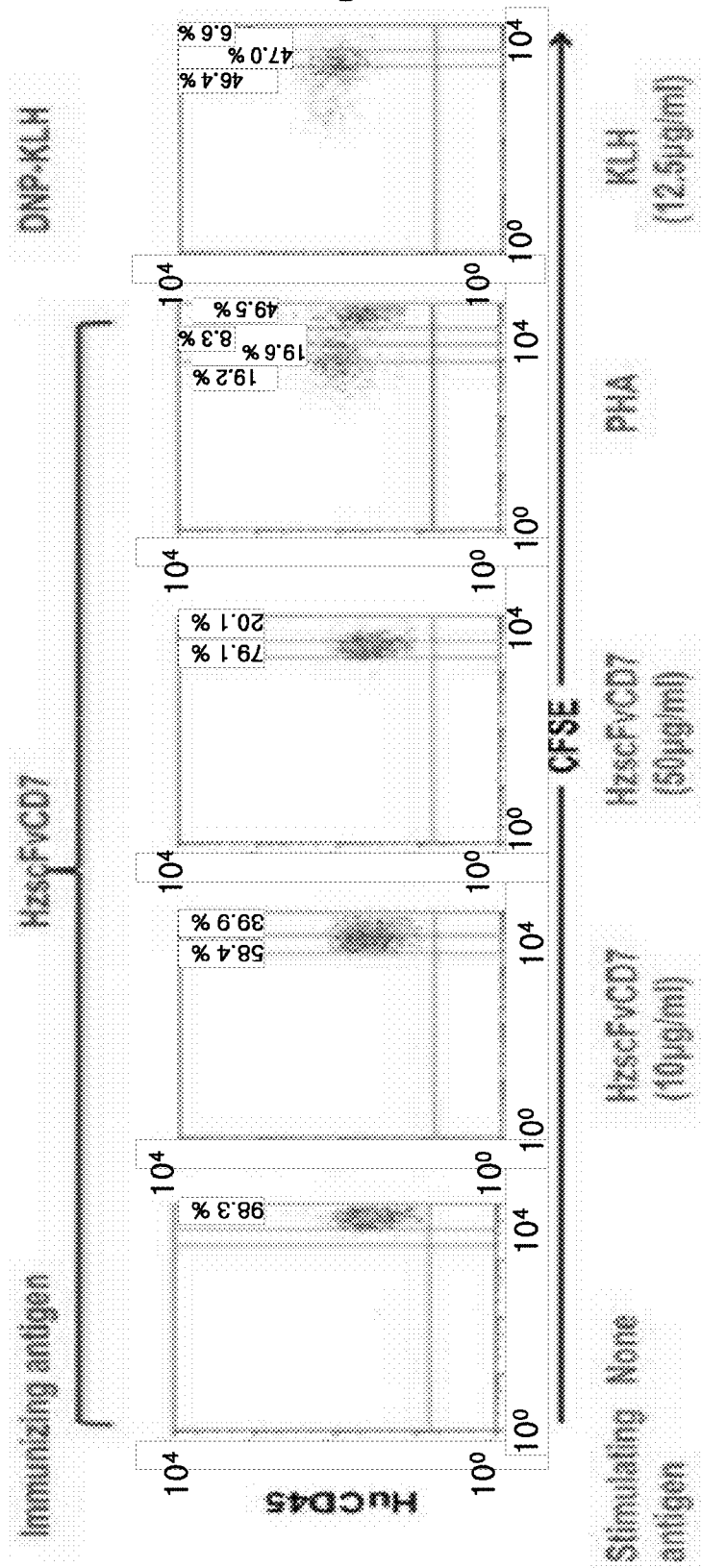
FIG. 19 shows graphs illustrating in vitro measurement results of antigenicity of HzscFvCD7 in the human body, by measuring the degree of differentiation of pancreatic cells after injecting HzscFvCD7 into humanized mouse (Hu-BLT).
Figure 20:
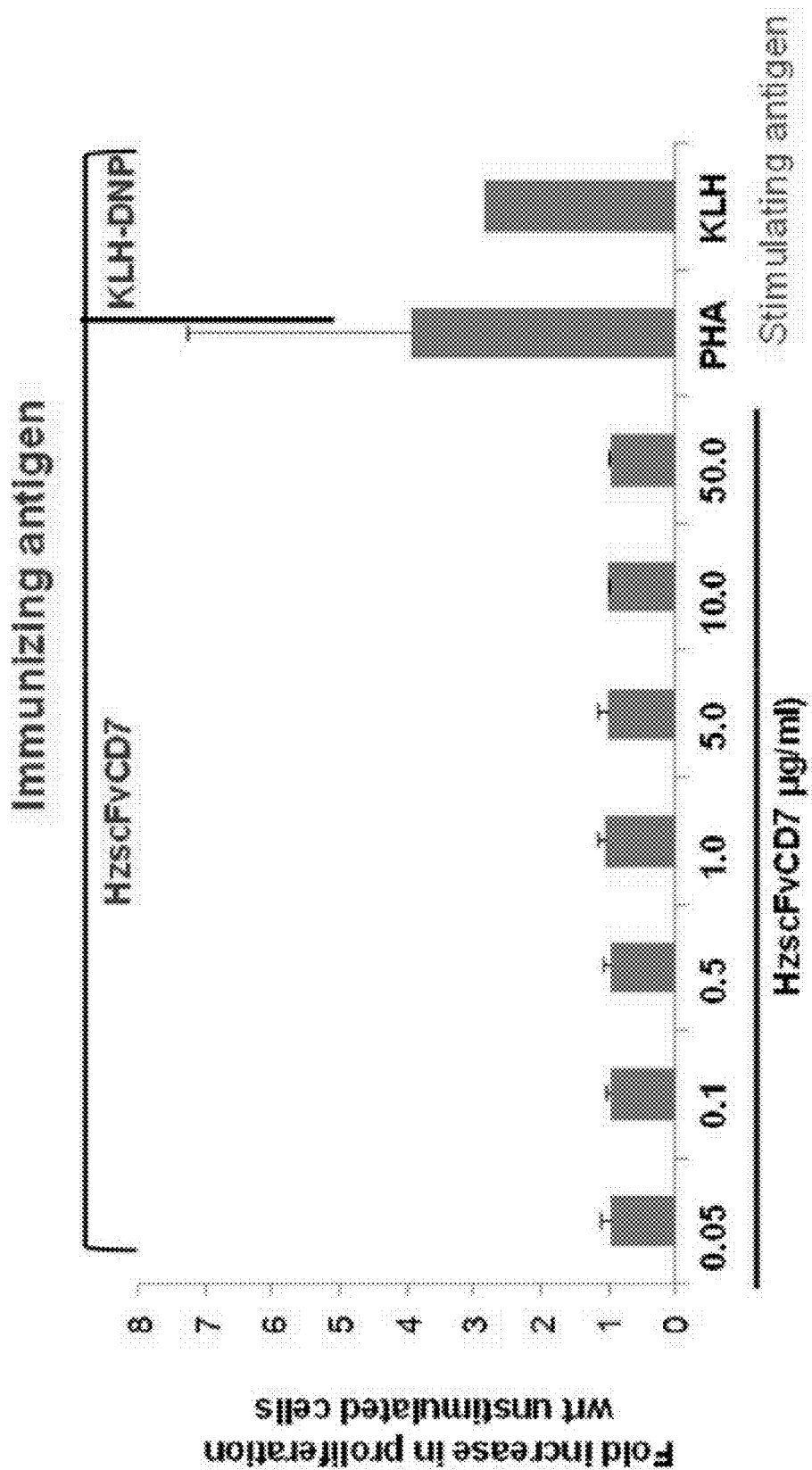
FIG. 20 is a graph illustrating in vitro measurement results of antigenicity of HzscFvCD7 in the human body, by measuring the degree of proliferation of pancreatic cells after HzscFvCD7 was injected into humanized mouse (Hu-BLT).

As a result, the cell differentiation (FIG. 19) and proliferation (FIG. 20) were much less induced in pancreatic cells derived from mice of the HzscFvCD7 treatment group rather than in pancreatic cells derived from mice of the DNP-KLH treatment group. It can be seen from the above results that HzscFvCD7 hardly caused the immune response in vivo as well as in vitro.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A human CD7-specific humanized scFv comprising a heavy chain variable region ($V_H$) composed of a polypeptide including the amino acid sequence represented by SEQ ID NO: 32, and a light chain variable region ($V_L$) composed of a polypeptide including the amino acid sequence represented by SEQ ID NO: 34.

2. The humanized scFv of claim 1, wherein the humanized scFv targets specifically to human CD7-expressing T cells.

3. The humanized scFv of claim 1, wherein the humanized scFv is composed of a polypeptide including the amino acid sequence represented by SEQ ID NO: 36.

4. An expression vector comprising a nucleotide sequence coding the humanized scFv of claim 1.

5. The expression vector of claim 4, wherein the expression vector includes the nucleotide sequence represented by SEQ ID NO: 37.

6. A carrier for delivering a T-cell activity regulator or a label specifically to T cells by targeting the T cells, the carrier comprising the humanized scFv of claim 1.

7. A composition containing a label fused to the N-terminal or C-terminal of the humanized scFv of claim 1.

8. A pharmaceutical composition for treating T cell-mediated diseases, the pharmaceutical composition containing a T-cell activity regulator fused to the N-terminal or C-terminal of the humanized scFv of claim 1, wherein said T-cell mediated diseases are selected from the group consisting of acquired immunodeficiency syndrome (AIDS), graft rejection, graft-versus-host diseases, unwanted delayed type of hypersensitivity reactions, T cell-mediated pulmonary diseases, autoimmune diseases, multiple sclerosis, neuritis, polymyositis, psoriasis, vitiligo, Siogren's syndrome, rheumatoid arthritis, type 1 diabetes, autoimmune pancreatitis inflammator bowel disease, Crohn's disease, ulcerative colitis, celiac disease, glomerulonephritis, scleroderma, sarcoidosis, autoimmune thyroid disease, Hashimoto's thyroiditis, Graves' disease, myasthenia pravis, Addison's disease, autoimmune uveoretinitis, pemphigus vulgaris, primary biliary cirrhosis, pernicious anemia, and systemic lupus erythematosus.

9. The pharmaceutical composition of claim 8, wherein the T-cell activity regulator is a T-cell activity inhibitor or a T-cell activity enhancer.

10. The pharmaceutical composition of claim 8, wherein the T-cell activity regulator is small interfering RAN (siRNA).

11. A method for treating T cell-mediated diseases, the method comprising administering to a subject a composition containing a pharmaceutically effective amount of a T-cell activity regulator fused on the N-terminal or C-terminal of the humanized scFv of claim 1, wherein said T-cell mediated diseases are selected from the group consisting of acquired immunodeficiency syndrome (AIDS), graft rejection, graft-versus-host diseases, unwanted delayed type of hypersensitivity reactions. T cell-mediated pulmonary diseases, autoimmune diseases, multiple sclerosis, neuritis, polymyositis, psoriasis, vitiligo, Sjogren's syndrome, rheumatoid arthritis, type 1 diabetes, autoimmune pancreatitis, inflammatory bowel disease, Crohn's disease, ulcerative colitis, celiac disease, glomerulonephritis, scleroderma, sarcoldosis, autoimmune thyroid disease, Hashimoto's thyroiditis, Graves' disease, myasthenia gravis, Addison's disease, autoimmune uveoretinitis, pemphigus vulgaris, primary biliary cirrhosis, pernicious anemia, and systemic lupus erythematosus.

12. The method of claim 11, wherein the T-cell activity regulator is a T-cell activity inhibitor or T-cell activity enhancer.

13. The method of claim 11, wherein the T-cell activity regulator is small interfering RAN (siRNA).

\* \* \* \* \*

SEQUENCE LISTING

```
<160> NUMBER OF SEQ ID NOS: 60

<210> SEQ ID NO 1
<211> LENGTH: 24
<212> TYPE: DNA
<213> ORGANISM: Artificial Sequence
<220> FEATURE:
<223> OTHER INFORMATION: primer for LHS39

<400> SEQUENCE: 1
gacgaattca ctctaaccat ggaa                                              24

<210> SEQ ID NO 2
<211> LENGTH: 17
<212> TYPE: DNA
<213> ORGANISM: Artificial Sequence
<220> FEATURE:
<223> OTHER INFORMATION: primer for HCleaderback

<400> SEQUENCE: 2
ggagtggaca cctgtag                                                      17

<210> SEQ ID NO 3
<211> LENGTH: 30
<212> TYPE: DNA
<213> ORGANISM: Artificial Sequence
<220> FEATURE:
<223> OTHER INFORMATION: forward primer for CD7H

<400> SEQUENCE: 3
acaggtgtcc tctccgaggt gcaactggtg                                        30

<210> SEQ ID NO 4
<211> LENGTH: 37
<212> TYPE: DNA
<213> ORGANISM: Artificial Sequence
<220> FEATURE:
<223> OTHER INFORMATION: reverse primer for CD7H

<400> SEQUENCE: 4
ccgatgggcc cttggtggag gccgaggaaa cggtgac                                37

<210> SEQ ID NO 5
<211> LENGTH: 24
<212> TYPE: DNA
<213> ORGANISM: Artificial Sequence
<220> FEATURE:
<223> OTHER INFORMATION: forward primer for CD7H1

<400> SEQUENCE: 5
tccctgagac tctcctgtgc agcc                                              24

<210> SEQ ID NO 6
<211> LENGTH: 24
<212> TYPE: DNA
<213> ORGANISM: Artificial Sequence
<220> FEATURE:
<223> OTHER INFORMATION: reverse primer for CD7H1

<400> SEQUENCE: 6
ggagagtctc agggaccccc cagg                                              24

<210> SEQ ID NO 7
<211> LENGTH: 30
<212> TYPE: DNA
<213> ORGANISM: Artificial Sequence
```

```
<220> FEATURE:
<223> OTHER INFORMATION: forward primer for CD7H2

<400> SEQUENCE: 7
gctccaggga aggggctgga gtgggtcgca                                    30

<210> SEQ ID NO 8
<211> LENGTH: 30
<212> TYPE: DNA
<213> ORGANISM: Artificial Sequence
<220> FEATURE:
<223> OTHER INFORMATION: reverse primer for CD7H2

<400> SEQUENCE: 8 cccctteccct ggagcctggc gaacccaaga                                   30

<210> SEQ ID NO 9
<211> LENGTH: 24
<212> TYPE: DNA
<213> ORGANISM: Artificial Sequence
<220> FEATURE:
<223> OTHER INFORMATION: forward primer for CD7H3

<400> SEQUENCE: 9
tactatgcag acagtgtgaa gggc                                          24

<210> SEQ ID NO 10
<211> LENGTH: 24
<212> TYPE: DNA
<213> ORGANISM: Artificial Sequence
<220> FEATURE:
<223> OTHER INFORMATION: reverse primer for CD7H3

<400> SEQUENCE: 10
actgtctgca tagtaggtga aacc                                          24

<210> SEQ ID NO 11
<211> LENGTH: 27
<212> TYPE: DNA
<213> ORGANISM: Artificial Sequence
<220> FEATURE:
<223> OTHER INFORMATION: forward primer for CD7H4

<400> SEQUENCE: 11
gccaagaaca gcctgtatct gcaaatg                                       27

<210> SEQ ID NO 12
<211> LENGTH: 27
<212> TYPE: DNA
<213> ORGANISM: Artificial Sequence
<220> FEATURE:
<223> OTHER INFORMATION: reverse primer for CD7H4

<400> SEQUENCE: 12
caggctgttc ttggcattat ctctgga                                       27

<210> SEQ ID NO 13
<211> LENGTH: 33
<212> TYPE: DNA
<213> ORGANISM: Artificial Sequence
<220> FEATURE:
<223> OTHER INFORMATION: forward primer for CD7H5

<400> SEQUENCE: 13
ctgagggctg aggacacggc cgtgtattac tgt                                33
```

<210> SEQ ID NO 14
<211> LENGTH: 36
<212> TYPE: DNA
<213> ORGANISM: Artificial Sequence
<220> FEATURE:
<223> OTHER INFORMATION: reverse primer for CD7H5

<400> SEQUENCE: 14
gtcctcagcc ctcagactgt tcatttgcag atacag                                 36

<210> SEQ ID NO 15
<211> LENGTH: 36
<212> TYPE: DNA
<213> ORGANISM: Artificial Sequence
<220> FEATURE:
<223> OTHER INFORMATION: reverse primer for CD7H6

<400> SEQUENCE: 15
cgaggaaacg gtgaccaggg tcccttggcc ccagac                                 36

<210> SEQ ID NO 16
<211> LENGTH: 21
<212> TYPE: DNA
<213> ORGANISM: Artificial Sequence
<220> FEATURE:
<223> OTHER INFORMATION: primer for LHS42

<400> SEQUENCE: 16
tgcaaagctt cggcacgagc a                                                 21

<210> SEQ ID NO 17
<211> LENGTH: 19
<212> TYPE: DNA
<213> ORGANISM: Artificial Sequence
<220> FEATURE:
<223> OTHER INFORMATION: primer for KCleaderback

<400> SEQUENCE: 17
tccttcaaca ccagacaac                                                    19

<210> SEQ ID NO 18
<211> LENGTH: 45
<212> TYPE: DNA
<213> ORGANISM: Artificial Sequence
<220> FEATURE:
<223> OTHER INFORMATION: forward primer for CD7L

<400> SEQUENCE: 18
tctggtgttg aaggagatat ccagatgaca cagagtccat cctcc                       45

<210> SEQ ID NO 19
<211> LENGTH: 31
<212> TYPE: DNA
<213> ORGANISM: Artificial Sequence
<220> FEATURE:
<223> OTHER INFORMATION: reverse primer for CD7L

<400> SEQUENCE: 19
agccaccgta cgttttattt ccaccttggt c                                      31

<210> SEQ ID NO 20
<211> LENGTH: 30
<212> TYPE: DNA
<213> ORGANISM: Artificial Sequence
<220> FEATURE:
<223> OTHER INFORMATION: forward primer for CD7L1

-continued

<400> SEQUENCE: 20
ggagacagag tcaccatcac ttgcagtgca                                      30

<210> SEQ ID NO 21
<211> LENGTH: 24
<212> TYPE: DNA
<213> ORGANISM: Artificial Sequence
<220> FEATURE:
<223> OTHER INFORMATION: reverse primer for CD7L1

<400> SEQUENCE: 21
ggtgactctg tctcccacag aggc                                            24

<210> SEQ ID NO 22
<211> LENGTH: 30
<212> TYPE: DNA
<213> ORGANISM: Artificial Sequence
<220> FEATURE:
<223> OTHER INFORMATION: forward primer for CD7L2

<400> SEQUENCE: 22
ccaggaaaag ttcctaaact cctgatctat                                      30

<210> SEQ ID NO 23
<211> LENGTH: 30
<212> TYPE: DNA
<213> ORGANISM: Artificial Sequence
<220> FEATURE:
<223> OTHER INFORMATION: reverse primer for CD7L2

<400> SEQUENCE: 23
tttaggaact tttcctggtt tctgctgata                                      30

<210> SEQ ID NO 24
<211> LENGTH: 33
<212> TYPE: DNA
<213> ORGANISM: Artificial Sequence
<220> FEATURE:
<223> OTHER INFORMATION: forward primer for CD7L3

<400> SEQUENCE: 24
agcagcctgc aacctgaaga tgttgccact tat                                  33

<210> SEQ ID NO 25
<211> LENGTH: 33
<212> TYPE: DNA
<213> ORGANISM: Artificial Sequence
<220> FEATURE:
<223> OTHER INFORMATION: reverse primer for CD7L3

<400> SEQUENCE: 25
aggttgcagg ctgctgatgg tgagagtata atc                                  33

<210> SEQ ID NO 26
<211> LENGTH: 34
<212> TYPE: DNA
<213> ORGANISM: Artificial Sequence
<220> FEATURE:
<223> OTHER INFORMATION: forward primer for scfv L-ndeI

<400> SEQUENCE: 26
caggatcgca tatggatatc cagatgacac agag                                 34

<210> SEQ ID NO 27

```
<210> SEQ ID NO 27
<211> LENGTH: 21
<212> TYPE: DNA
<213> ORGANISM: Artificial Sequence
<220> FEATURE:
<223> OTHER INFORMATION: reverse primer for scfv L

<400> SEQUENCE: 27
accaccacgt tttatttcca c                                            21

<210> SEQ ID NO 28
<211> LENGTH: 16
<212> TYPE: DNA
<213> ORGANISM: Artificial Sequenc
<220> FEATURE:
<223> OTHER INFORMATION: forward primer for linker

<400> SEQUENCE: 28
ataaaacgtg gtggtg                                                  16

<210> SEQ ID NO 29
<211> LENGTH: 18
<212> TYPE: DNA
<213> ORGANISM: Artificial Sequence
<220> FEATURE:
<223> OTHER INFORMATION: reverse primer for linker

<400> SEQUENCE: 29
ttgcacctcg gatccacc                                                18

<210> SEQ ID NO 30
<211> LENGTH: 24
<212> TYPE: DNA
<213> ORGANISM: Artificial Sequence
<220> FEATURE:
<223> OTHER INFORMATION: forward primer for scfv H

<400> SEQUENCE: 30
ggtggatccg aggtgcaact ggtg                                         24

<210> SEQ ID NO 31
<211> LENGTH: 27
<212> TYPE: DNA
<213> ORGANISM: Artificial Sequence
<220> FEATURE:
<223> OTHER INFORMATION: reverse primer for scfv H-XhoI

<400> SEQUENCE: 31
tagtgcctcg agaggtcaag cttacta                                      27

<210> SEQ ID NO 32
<211> LENGTH: 117
<212> TYPE: PRT
<213> ORGANISM: Artificial Sequence
<220> FEATURE:
<223> OTHER INFORMATION: designed humanized VH

<400> SEQUENCE: 32

Glu Val Gln Leu Val Glu Ser Gly Gly Gly Leu Val Lys Pro Gly Gly
1               5                   10                  15

Ser Leu Arg Leu Ser Cys Ala Ala Ser Gly Leu Thr Phe Ser Ser Tyr
            20                  25                  30

Ala Met Ser Trp Val Arg Gln Ala Pro Gly Lys Gly Leu Glu Trp Val
        35                  40                  45

Ala Ser Ile Ser Ser Gly Gly Phe Thr Tyr Tyr Ala Asp Ser Val Lys
    50                  55                  60
```

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Asp Glu Val Arg Gly Tyr Leu Asp Val Trp Gly Gln Gly Thr Leu
            100                 105                 110

Val Thr Val Ser Ser
        115

<210> SEQ ID NO 33
<211> LENGTH: 351
<212> TYPE: DNA
<213> ORGANISM: Artificial Sequence
<220> FEATURE:
<223> OTHER INFORMATION: designed humanized VH

<400> SEQUENCE: 33
gaggtgcaac tggtggagtc tgggggtggc ttagtgaagc ctgggggtc cctgagactc      60 tcctgtgcag cctctggact cactttcagt agctatgcca tgtcttgggt tcgccaggct    120
ccagggaagg gctggagtg gtcgcatcc attagtagtg gtggtttcac ctactatgca     180
gacagtgtga agggccgatt caccatctcc agagataatg ccaagaacag cctgtatctg    240
caaatgaaca gtctgagggc tgaggacacg gccgtgtatt actgtgcaag agacgaggta    300
cgggggtacc tcgatgtctg gggccaaggg accctggtca ccgtttcctc g             351

<210> SEQ ID NO 34
<211> LENGTH: 107
<212> TYPE: PRT
<213> ORGANISM: Artificial Sequence
<220> FEATURE:
<223> OTHER INFORMATION: designed humanized VL

<400> SEQUENCE: 34

Asp Ile Gln Met Thr Gln Ser Pro Ser Ser Leu Ser Ala Ser Leu Gly
1               5                   10                  15

Asp Arg Val Thr Ile Thr Cys Ser Ala Ser Gln Gly Ile Ser Asn Tyr
            20                  25                  30

Leu Asn Trp Tyr Gln Gln Lys Pro Gly Lys Val Pro Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Gln Gln Tyr Ser Lys Leu Pro Tyr
                85                  90                  95

Thr Phe Gly Gly Gly Thr Lys Val Glu Ile Lys
            100                 105

<210> SEQ ID NO 35
<211> LENGTH: 321
<212> TYPE: DNA
<213> ORGANISM: Artificial Sequence
<220> FEATURE:
<223> OTHER INFORMATION: designed humanized VL

<400> SEQUENCE: 35
gatatccaga tgacacagag tccatcctcc ctgtctgcct ctctgggaga cagagtcacc      60
atcacttgca gtgcaagtca gggcattagc aattatttaa actggtatca gcagaaacca    120

```
ggaaaagttc ctaaactcct gatctattac acatcaagtt tacactcagg agtcccatca      180
aggttcagtg gcagtgggtc tgggacagat tatactctca ccatcagcag cctgcaacct      240
gaagatgttg ccacttatta ttgtcagcag tatagcaagc ttccgtacac gttcggaggg      300
gggaccaagg tggaaataaa a                                                321
```

<210> SEQ ID NO 36
<211> LENGTH: 257
<212> TYPE: PRT
<213> ORGANISM: Artificial Sequence
<220> FEATURE:
<223> OTHER INFORMATION: full length amino acid sequence of HzscfvCD7

<400> SEQUENCE: 36

```
Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Gly Ile Ser Asn Tyr
                20                  25                  30

Leu Asn Trp Tyr Gln Gln Lys Pro Gly Lys Val Pro Lys Leu Leu Ile
            35                  40                  45

Tyr Tyr Thr Ser Ser Leu His Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Gln Gln Tyr Ser Lys Leu Pro Tyr
                85                  90                  95

Thr Phe Gly Gly Gly Thr Lys Val Glu Ile Lys Arg Gly Gly Gly Gly
            100                 105                 110

Ser Gly Gly Gly Gly Ser Gly Gly Gly Ser Gly Gly Gly Gly Ser
        115                 120                 125

Glu Val Gln Leu Val Glu Ser Gly Gly Gly Leu Val Lys Pro Gly Gly
130                 135                 140

Ser Leu Arg Leu Ser Cys Ala Ala Ser Gly Leu Thr Phe Ser Ser Tyr
145                 150                 155                 160

Ala Met Ser Trp Val Arg Gln Ala Pro Gly Lys Gly Leu Glu Trp Val
                165                 170                 175

Ala Ser Ile Ser Ser Gly Gly Phe Thr Tyr Tyr Ala Asp Ser Val Lys
            180                 185                 190

Gly Arg Phe Thr Ile Ser Arg Asp Asn Ala Lys Asn Ser Leu Tyr Leu
        195                 200                 205

Gln Met Asn Ser Leu Arg Ala Glu Asp Thr Ala Val Tyr Tyr Cys Ala
    210                 215                 220

Arg Asp Glu Val Arg Gly Tyr Leu Asp Val Trp Gly Gln Gly Thr Leu
225                 230                 235                 240

Val Thr Val Ser Ser Ala Ser Gly Ala Asp His His His His His
                245                 250                 255

Cys
```

<210> SEQ ID NO 37
<211> LENGTH: 771
<212> TYPE: DNA
<213> ORGANISM: Artificial Sequence
<220> FEATURE:
<223> OTHER INFORMATION: full length nucleotide sequence coding for
      HzscfvCD7

<400> SEQUENCE: 37

```
gatatccaga tgacacagag tccatcctcc ctgtctgcct ctgtgggaga cagagtcacc    60
atcacttgca gtgcaagtca gggcattagc aattatttaa actggtatca gcagaaacca   120
ggaaaagttc ctaaactcct gatctattac acatcaagtt tacactcagg agtcccatca   180
aggttcagtg gcagtgggtc tgggacagat tatactctca ccatcagcag cctgcaacct   240
gaagatgttg ccacttatta ttgtcagcag tatagcaagc ttccgtacac gttcggaggg   300
gggaccaagg tggaaataaa acgtggtggt ggtggttctg gtggtggtgg ttctggcggc   360
ggcggctccg gtggtggtgg atccgagtg caactggtgg agtctggggg tggcttagtg   420
aagcctgggg gtccctgag actctcctgt gcagcctctg gactcacttt cagtagctat   480
gccatgtctt gggttcgcca ggctccaggg aaggggctgg agtgggtcgc atccattagt   540
agtggtggtt tcacctacta tgcagacagt gtgaagggcc gattcaccat ctccagagat   600
aatgccaaga acagcctgta tctgcaaatg aacagtctga gggctgagga cacggccgtg   660
tattactgtg caagagacga ggtacggggg tacctcgatg tctggggcca agggaccctg   720
gtcaccgttt cctcggcctc gggggccgat caccatcatc accatcattg c             771
```

<210> SEQ ID NO 38
<211> LENGTH: 57
<212> TYPE: DNA
<213> ORGANISM: Artificial Sequence
<220> FEATURE:
<223> OTHER INFORMATION: signal sequence of VH

<400> SEQUENCE: 38

```
atggaatgga gctgggtctt tctcttcttc ctgtcagtaa ctacaggtgt cctctcc    57
```

<210> SEQ ID NO 39
<211> LENGTH: 351
<212> TYPE: DNA
<213> ORGANISM: Artificial Sequence
<220> FEATURE:
<223> OTHER INFORMATION: VH of muscfvCD7

<400> SEQUENCE: 39

```
gaggtgcaac tggtggagtc tgggggtggc ttagtgaagc ctgggggtc cctgagactc    60 tcctgtgcag cctctggact cactttcagt agctatgcca tgtcttgggt tcgccaggct   120
ccagggaagg gctggagtg gtcgcatcc attagtagtg gtggtttcac ctactatgca   180
gacagtgtga agggccgatt caccatctcc agagataatg ccaagaacag cctgtatctg   240
caaatgaaca gtctgagggc tgaggacacg gccgtgtatt actgtgcaag agacgaggta   300 cggggggtacc tcgatgtctg gggccaaggg accctggtca ccgtttcctc g           351
```

<210> SEQ ID NO 40
<211> LENGTH: 63
<212> TYPE: DNA
<213> ORGANISM: Artificial Sequence
<220> FEATURE:
<223> OTHER INFORMATION: Humanized VH fragment 1

<400> SEQUENCE: 40

```
gaggtgcaac tggtggagtc tgggggtggc ttagtgaagc ctgggggtc cctgagactc    60 tcc                                                                   63
```

<210> SEQ ID NO 41
<211> LENGTH: 84
<212> TYPE: DNA

```
<213> ORGANISM: Artificial Sequence
<220> FEATURE:
<223> OTHER INFORMATION: Humanized VH fragment 2

<400> SEQUENCE: 41
tccctgagac tctcctgtgc agcctctgga ctcactttca gtagctatgc catgtcttgg    60
gttcgccagg ctccagggaa gggg                                           84

<210> SEQ ID NO 42
<211> LENGTH: 69
<212> TYPE: DNA
<213> ORGANISM: Artificial Sequence
<220> FEATURE:
<223> OTHER INFORMATION: Humanized VH fragment 3

<400> SEQUENCE: 42
gctccaggga aggggctgga gtgggtcgca tccattagta gtggtggttt cacctactat    60
gcagacagt                                                            69

<210> SEQ ID NO 43
<211> LENGTH: 63
<212> TYPE: DNA
<213> ORGANISM: Artificial Sequence
<220> FEATURE:
<223> OTHER INFORMATION: Humanized VH fragment 4

<400> SEQUENCE: 43
tactatgcag acagtgtgaa gggccgattc accatctcca gagataatgc caagaacagc    60
ctg                                                                  63

<210> SEQ ID NO 44
<211> LENGTH: 48
<212> TYPE: DNA
<213> ORGANISM: Artificial Sequence
<220> FEATURE:
<223> OTHER INFORMATION: Humanized VH fragment 5

<400> SEQUENCE: 44
gccaagaaca gcctgtatct gcaaatgaac agtctgaggg ctgaggac                 48

<210> SEQ ID NO 45
<211> LENGTH: 99
<212> TYPE: DNA
<213> ORGANISM: Artificial Sequence
<220> FEATURE:
<223> OTHER INFORMATION: Humanized VH fragment 6

<400> SEQUENCE: 45
ctgagggctg aggacacggc cgtgtattac tgtgcaagag acgaggtacg ggggtacctc    60
gatgtctggg gccaagggac cctggtcacc gtttcctcg                           99

<210> SEQ ID NO 46
<211> LENGTH: 186
<212> TYPE: DNA
<213> ORGANISM: Artificial Sequence
<220> FEATURE:
<223> OTHER INFORMATION: Humanized VH fragment 1-1

<400> SEQUENCE: 46
gaggtgcaac tggtggagtc tgggggtggc ttagtgaagc ctgggggtc cctgagactc     60 tcctgtgcag cctctggact cactttcagt agctatgcca tgtcttggt tcgccaggct    120 ccagggaagg ggctggagtg ggtcgcatcc attagtagtg tggtttcac ctactatgca    180
``` gacagt                                                                          186

<210> SEQ ID NO 47
<211> LENGTH: 180
<212> TYPE: DNA
<213> ORGANISM: Artificial Sequence
<220> FEATURE:
<223> OTHER INFORMATION: Humanized VH fragment 1-2

<400> SEQUENCE: 47
tactatgcag acagtgtgaa gggccgattc accatctcca gagataatgc caagaacagc     60
ctgtatctgc aaatgaacag tctgagggct gaggacacgg ccgtgtatta ctgtgcaaga    120
gacgaggtac gggggtacct cgatgtctgg ggccaaggga ccctggtcac cgtttcctcg    180

<210> SEQ ID NO 48
<211> LENGTH: 60
<212> TYPE: DNA
<213> ORGANISM: Artificial Sequence
<220> FEATURE:
<223> OTHER INFORMATION: signal sequence of VK

<400> SEQUENCE: 48
atggagacac attctcaggt ctttgtatac atgttgctgt ggttgtctgg tgttgaagga     60

<210> SEQ ID NO 49
<211> LENGTH: 321
<212> TYPE: DNA
<213> ORGANISM: Artificial Sequence
<220> FEATURE:
<223> OTHER INFORMATION: VK of muscfvCD7

<400> SEQUENCE: 49
gatatccaga tgacacagag tccatcctcc ctgtctgcct ctctgggaga cagagtcacc     60
atcacttgca gtgcaagtca gggcattagc aattatttaa actggtatca gcagaaacca    120
ggaaaagttc ctaaactcct gatctattac acatcaagtt acactcagg agtcccatca    180 aggttcagtg gcagtgggtc tgggacagat tatactctca ccatcagcag cctgcaacct    240
gaagatgttg ccacttatta ttgtcagcag tatagcaagc ttccgtacac gttcggaggg    300
gggaccaagg tggaaataaa a                                              321

<210> SEQ ID NO 50
<211> LENGTH: 60
<212> TYPE: DNA
<213> ORGANISM: Artificial Sequence
<220> FEATURE:
<223> OTHER INFORMATION: Humanized VK fragment 1

<400> SEQUENCE: 50
gatatccaga tgacacagag tccatcctcc ctgtctgcct ctctgggaga cagagtcacc     60

<210> SEQ ID NO 51
<211> LENGTH: 90
<212> TYPE: DNA
<213> ORGANISM: Artificial Sequence
<220> FEATURE:
<223> OTHER INFORMATION: Humanized VK fragment 2

<400> SEQUENCE: 51
ggagacagag tcaccatcac ttgcagtgca agtcagggca ttagcaatta tttaaactgg     60
tatcagcaga aaccaggaaa agttcctaaa                                      90

<210> SEQ ID NO 52
<211> LENGTH: 126
<212> TYPE: DNA
<213> ORGANISM: Artificial Sequence
<220> FEATURE:
<223> OTHER INFORMATION: Humanized VK fragment 3

<400> SEQUENCE: 52

```
ccaggaaaag ttcctaaact cctgatctat tacacatcaa gtttacactc aggagtccca      60
tcaaggttca gtggcagtgg gtctgggaca gattatactc tcaccatcag cagcctgcaa     120
cctgaa                                                                126
```

<210> SEQ ID NO 53
<211> LENGTH: 96
<212> TYPE: DNA
<213> ORGANISM: Artificial Sequence
<220> FEATURE:
<223> OTHER INFORMATION: Humanized VK fragment 4

<400> SEQUENCE: 53

```
agcagcctgc aacctgaaga tgttgccact tattattgtc agcagtatag caagcttccg      60
tacacgttcg agggggggac caaggtggaa ataaaa                                96
```

<210> SEQ ID NO 54
<211> LENGTH: 135
<212> TYPE: DNA
<213> ORGANISM: Artificial Sequence
<220> FEATURE:
<223> OTHER INFORMATION: Humanized VK fragment 1-1

<400> SEQUENCE: 54

```
gatatccaga tgacacagag tccatcctcc ctgtctgcct ctctgggaga cagagtcacc      60
atcacttgca gtgcaagtca gggcattagc aattatttaa actggtatca gcagaaacca     120
ggaaaagttc ctaaa                                                      135
```

<210> SEQ ID NO 55
<211> LENGTH: 204
<212> TYPE: DNA
<213> ORGANISM: Artificial Sequence
<220> FEATURE:
<223> OTHER INFORMATION: Humanized VK fragment 1-2

<400> SEQUENCE: 55

```
ccaggaaaag ttcctaaact cctgatctat tacacatcaa gtttacactc aggagtccca      60
tcaaggttca gtggcagtgg gtctgggaca gattatactc tcaccatcag cagcctgcaa     120
cctgaagatg ttgccactta ttattgtcag cagtatagca agcttccgta cacgttcgga     180 gggggggacca aggtggaaat aaaa                                           204
```

<210> SEQ ID NO 56
<211> LENGTH: 63
<212> TYPE: DNA
<213> ORGANISM: Artificial Sequence
<220> FEATURE:
<223> OTHER INFORMATION: linker of scFv

<400> SEQUENCE: 56

```
cgtggtggtg gtggttctgg tggtggtggt tctggcggcg gcggctccgg tggtggtgga      60
tcc                                                                    63
```

<210> SEQ ID NO 57

```
<211> LENGTH: 117
<212> TYPE: PRT
<213> ORGANISM: Artificial Sequence
<220> FEATURE:
<223> OTHER INFORMATION: VH of muscfvCD7

<400> SEQUENCE: 57

Glu Val Gln Leu Val Glu Ser Gly Gly Gly Leu Val Lys Pro Gly Gly
1               5                   10                  15

Ser Leu Lys Leu Ser Cys Ala Ala Ser Gly Leu Thr Phe Ser Ser Tyr
            20                  25                  30

Ala Met Ser Trp Val Arg Gln Thr Pro Glu Lys Arg Leu Glu Trp Val
        35                  40                  45

Ala Ser Ile Ser Ser Gly Gly Phe Thr Tyr Tyr Pro Asp Ser Val Lys
    50                  55                  60

Gly Arg Phe Thr Ile Ser Arg Asp Asn Ala Arg Asn Ile Leu Tyr Leu
65                  70                  75                  80

Gln Met Ser Ser Leu Arg Ser Glu Asp Thr Ala Met Tyr Tyr Cys Ala
                85                  90                  95

Arg Asp Glu Val Arg Gly Tyr Leu Asp Val Trp Gly Ala Gly Thr Thr
            100                 105                 110

Val Thr Val Ser Ser
        115

<210> SEQ ID NO 58
<211> LENGTH: 107
<212> TYPE: PRT
<213> ORGANISM: Artificial Sequence
<220> FEATURE:
<223> OTHER INFORMATION: VL of muscfvCD7

<400> SEQUENCE: 58

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ser Lys Leu Pro Tyr
                85                  90                  95

Thr Phe Gly Gly Gly Ile Lys Leu Glu Ile Lys
            100                 105

<210> SEQ ID NO 59
<211> LENGTH: 117
<212> TYPE: PRT
<213> ORGANISM: Artificial Sequence
<220> FEATURE:
<223> OTHER INFORMATION: VH of IGHV3-h*01 (P)

<400> SEQUENCE: 59

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30
```

```
Tyr Met Asn Trp Val Arg Gln Ala Pro Gly Lys Gly Leu Glu Trp Val
        35                  40                  45

Ser Ser Ile Ser Ser Ser Thr Ile Tyr Tyr Ala Asp Ser Val Lys
    50                  55                  60

Gly Arg Phe Thr Ile Ser Arg Asp Asn Ala Lys Asn Ser Leu Tyr Leu
 65              70                  75                      80

Gln Met Asn Ser Leu Arg Ala Glu Asp Thr Ala Val Tyr Tyr Cys Ala
                85                  90                  95

Arg Asp Glu Val Arg Gly Tyr Leu Asp Val Trp Gly Gln Gly Thr Leu
            100                 105                 110

Val Thr Val Ser Ser
        115

<210> SEQ ID NO 60
<211> LENGTH: 107
<212> TYPE: PRT
<213> ORGANISM: Artificial Sequence
<220> FEATURE:
<223> OTHER INFORMATION: VL of IGKV1-27*01

<400> SEQUENCE: 60

Asp Ile Gln Met Thr Gln Ser Pro Ser Ser Leu Ser Ala Ser Val Gly
 1               5                  10                      15

Asp Arg Val Thr Ile Thr Cys Arg Ala Ser Gln Gly Ile Ser Ala Tyr
            20                  25                  30

Leu Asn Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
 65              70                  75                      80

Glu Asp Val Ala Thr Tyr Tyr Cys Gln Lys Tyr Asn Ser Ala Pro Tyr
                85                  90                  95

Thr Phe Gly Gly Gly Ile Lys Val Glu Ile Lys
            100                 105
```